(12) United States Patent
Bortis et al.

(10) Patent No.: US 12,100,519 B2
(45) Date of Patent: Sep. 24, 2024

(54) PEER-TO-PEER SECURE AND SCALABLE NETWORK ARCHITECTURE

(71) Applicant: The Health Utility Network, Inc., Chicago, IL (US)

(72) Inventors: Gerald Bortis, Rancho Santa Margarita, CA (US); Aaron Jones, Roswell, GA (US); Calin Alexandru Morar, Phoenix, AZ (US); Gabriela Pelin, Winter Park, FL (US); Daniel Sanders, Canton, GA (US); Gary Brian Word, Franklin, TN (US)

(73) Assignee: The Health Utility Network, Inc., Chicago, IL (US)

( * ) Notice: Subject to any disclaimer, the term of this patent is extended or adjusted under 35 U.S.C. 154(b) by 0 days.

(21) Appl. No.: 18/458,954

(22) Filed: Aug. 30, 2023

(65) Prior Publication Data
US 2024/0071633 A1 Feb. 29, 2024

Related U.S. Application Data

(60) Provisional application No. 63/402,923, filed on Aug. 31, 2022.

(51) Int. Cl.
*H04L 67/10* (2022.01)
*G16H 80/00* (2018.01)
(Continued)

(52) U.S. Cl.
CPC .............. *G16H 80/00* (2018.01); *H04L 9/50* (2022.05); *H04L 63/0272* (2013.01); *H04L 67/10* (2013.01)

(58) Field of Classification Search
CPC ........ H04L 9/50; H04L 63/0272; H04L 67/10
See application file for complete search history.

(56) References Cited

U.S. PATENT DOCUMENTS 11,600,395 B1 * 3/2023 Dent ...................... H04W 12/08
2018/0294047 A1 * 10/2018 Hosseini ................ G16B 50/30
(Continued)

OTHER PUBLICATIONS

The Health Utility Network, Inc. d/b/a Avaneer Health, PCT/IB2023/058640, International Search Report and Written Opinion, Dec. 7, 2023, 18 pgs.
(Continued)

*Primary Examiner* — Hua Fan
(74) *Attorney, Agent, or Firm* — Morgan, Lewis & Bockius LLP

(57) ABSTRACT

The various implementations described herein include methods and systems for configuring, managing, and/or using a health utility network. A system includes a health utility platform configured to execute collaboration services and distributed ledger services. The system also includes a health network including a private network interconnect configured to provide access, routing and service discovery. The health network is communicatively coupled to the health utility platform. The system also includes landing zones communicatively coupled to the health utility platform via the health network. Each landing zone is configured to run applications for a participant. The applications are configured to consume data and/or provide services on the health network. The collaboration services and the distributed ledger services are configured to provide context or facilitate data exchanges between different landing zones.

11 Claims, 12 Drawing Sheets

(51) Int. Cl.
*H04L 9/00* (2022.01)
*H04L 9/40* (2022.01)

(56) References Cited

U.S. PATENT DOCUMENTS

2019/0237169 A1    8/2019   Culver et al.
2021/0280306 A1    9/2021   Fairless et al.
2023/0395208 A1*  12/2023   Konyala ................ G16H 10/60

OTHER PUBLICATIONS

Anonymous: "SD-WAN—Wikipedia", Jan. 4, 2018 (Jan. 4, 2018), 9 pgs, XP93105039, [retrieved on Nov. 23, 2023], Retrieved from the Internet: URL:https://en.wikipedia.org/w/index.php?title=SD-WAN&oldid=818681663.

* cited by examiner

PEER-TO-PEER SECURE AND SCALABLE NETWORK ARCHITECTURE

PRIORITY CLAIM

This application claims priority to U.S. Provisional Patent Application No. 63/402,923, filed Aug. 31, 2022, which is hereby incorporated by reference in its entirety.

TECHNICAL FIELD

The disclosed implementations relate generally to healthcare applications, and more particularly, to methods and systems for peer-to-peer secure and scalable network architecture.

BACKGROUND

The healthcare industry has lagged in adopting new technologies. There is high fragmentation in the industry as electronic health records (EHRs) and other back-office systems from different players do not easily communicate with each other, if at all. At least 70% of health-care providers still exchange medical information by fax. The COVID pandemic has accelerated digitization, and the market is on the brink of automating broken processes with costly workarounds. Some standardization efforts, such as Fast Healthcare Interoperability Resources (FHIR), a Health Level Seven International (HL7) standard (HL7/FAST initiative), are beginning to show promise. Although there are initiatives accelerating standardization on FHIR and patient access to their data, they still assume marginal improvement in a point-to-point request/response model and therefore are not enough to free the healthcare system from the constraints of the broken care experience for people and their families. These initiatives also do not address the problems of data silos and lack of data fluidity, and the exorbitant amount of money that is spent on administration (e.g., up to 5 time more per capita in the United States compared to Canada and western Europe) without any tangible improvements in outcomes. As the population ages and chronic diseases spend increases, keeping up the administrative burden is becoming an impediment to improving health outcome. Care is personalized and situational and coordinated care cannot be effectively delivered within a technologically fragmented system. The healthcare companies that are responsible for care administration and delivery need to work together and put aside misaligned incentives.

In today's healthcare paradigm, it is complex to answer even simple questions. Consider the following example interaction between a provider and patient in conventional systems.
- Question: Who is this patient?
- Answer: Ask the patient to fill out forms
- Question: Is the patient currently covered?
- Answer: Ask the patient for the insurance ID card, make a copy, manually enter into the electronic health record (EHR) system.
- Question: What are the patient's medications, labs, imaging, and clinical history?
- Answer: Ask the patient and rely on what they know and remember to share Conventional systems rely on manual and electronic administrative processes to send/receive data between multiple providers and multiple payers. Today's processes are slow, expensive, and frustrating. Currently, over 60 billion faxes are sent each year. Patients are forced to fill out paperwork with same information time after time, processes are slow, manual, and have several opportunities for error (e.g., typos, identifying the wrong John Smith, etc.) While the average is about 4 eligibility checks for a visit, it is not uncommon that 10 to 14 eligibility checks are made for some healthcare interactions in today's environment.

Conventional techniques for addressing the challenge of sharing data are either of the "request/response" type, the data aggregation type, or the intermediary type. In request/response type interactions, the data is requested by one organization and the responder sends a copy of the data to the requester after confirming the requester has a right to the data. The data that is sent is a copy at the time of the response. If the data changes, the responder typically has no obligation to send the updated data. In the data aggregation type, one company receives data from multiple organizations and creates an aggregated database of all the data collected. The aggregated data can provide a dataset for analysis, typically with the patient information hidden. Patients are not directly helped by this aggregated data, as their identity is no longer associated with their data. The intermediary type is one that acts as a go-between for providers and payers, taking data in and providing it to another organization. Many times, that intermediary will provide a service to change the format of the data to match what the receiving organization expects. This is caused by the organizations not having a common standard for data but instead each having a variation of the X12 EDI healthcare data formats.

SUMMARY

Healthcare needs an innovative digital landscape that relies on standardized technology stacks, secure interconnected compute environments, common data standards and data models. Healthcare also needs an expandable set of distributed solutions that can make use of these environments to reduce administrative burden and improve health outcome. At least some of the problems described above may be addressed by the techniques described herein. Systems according to these techniques may be used to implement a peer-to-peer secure and scalable network that can guarantee transactional integrity. Such systems may provide the opportunity to radically re-engineer many of the healthcare processes, particularly those that process administrative data. Such concepts may be used to implement standardized workspaces for healthcare organizations to communicate more easily, embrace competition and develop common standardized and efficient processes for back-office administration. Some implementations enable fast and secure data access and exchange between the parties involved in a person's care on secure infrastructure. Some implementations include a secure data highway that connects the healthcare back offices between payers, providers, and financial institutions to address at least some of the problems described above. By standardizing the fragmented administrative processes and disjointed data models into common processes and data models for payers and providers, many of the challenges described above may be addressed. These standardized processes and data models may help generate savings through development of distributed solutions that provide more efficient administrative processes with less errors and the retirement of current systems, processes and data model and the transitioning to infrastructure with secure interoperable data exchange between and among components of one or more distributed solutions as described herein.

In accordance with some implementations, a system includes a health utility platform configured to execute one or more collaboration services and one or more distributed ledger services. The health network includes a private network interconnect configured to provide access, routing, and service discovery. The health network is communicatively coupled to the health utility platform. The system also includes a plurality of landing zones communicatively coupled to the health utility platform via the health network. Each landing zone is configured to run one or more applications for a participant. The one or more applications are configured to consume data and/or provide services on the health network. The one or more collaboration services and the one or more distributed ledger services are configured to provide immutable audit trails, to provide context or facilitate data exchanges between different landing zones of the plurality of landing zones, and to provide execution services for applications that run partially or completely on a distributed ledger.

In some implementations, each landing zone is configured in a virtual private cloud, as a set of components running in an environment for running containers.

In some implementations, each landing zone includes at least a cross-platform interface engine, a Health Level Seven (HL7) Fast Healthcare Interoperability Resources (FHIR) server, a data storage, a lightweight web server, an authentication and authorization tool, and access to one or more blockchain services.

In some implementations, the one or more collaboration services include an identity service configured to generate a unique identifier for each member, based on deterministic and/or probabilistic matching.

In some implementations, the one or more collaboration services include a data discovery service configured to provide a standardized resource-based directory service for identifying the location of data corresponding to a member, such as through the use of FHIR servers.

In some implementations, the one or more collaboration services include a workflow authorization service configured to perform authorization based on a plurality of levels of granularity, including data source, resource type and requesting entity.

In some implementations, the one or more collaboration services include a workflow authorization service configured to authorize access to a data highway for accessing data stored in the health network by participants who have a valid Health Insurance Portability and Accountability Act (HIPAA) reason to access the data.

In some implementations, the one or more collaboration services are implemented using one or more representational state transfer (RESTful) APIs.

In some implementations, the one or more collaboration services are configured in one or several virtual private clouds, as a set of components running in an environment for running containers.

In some implementations, the one or more distributed ledger services are configured to run one or more blockchain services.

In some implementations, the blockchain service includes (i) a first one or more nodes configured to store copies of a blockchain and perform chaincode or smart contract execution and transaction validation and (ii) a second one or more nodes configured to provide an ordering service which determines the ordering of blocks on the blockchain and enforces access controls to channels. A channel is a virtual blockchain where resources including transactions and smart contracts are only accessible by members of the channel.

In some implementations, the one or more distributed ledger services are configured to run smart contracts, including a smart contract to pin hashes of transactions to provide immutable audit trails.

In some implementations, each landing zone is configured as a virtual machine with identical tools deployed in automatically horizontally and vertically scalable compute and storage environments.

In some implementations, each landing zone is configured to increase a number of compute engines to satisfy a surge in demand.

In some implementations, the health network is configured based on a software-defined wide area network (SD-WAN) model to use a plurality of connectivity mediums and to overlay network service over one or more networks.

In some implementations, the health network is configured to provide connections of different types and is multi-site and multi-cloud capable.

In some implementations, the health network is configured to encrypt overlay traffic and control application protocols.

In some implementations, each landing zone is communicatively coupled to a respective on-premises system of a participant in the network and is configured to provide or consume data and/or internal services.

In some implementations, each landing zone is communicatively coupled to one or more cloud services configured for Big Data management and analytics.

In some implementations, each landing zone is configured to connect with a participant source system for a respective participant via a secure connection, such as a site-to-site VPN connection or a private link connection.

In some implementations, the one or more collaboration services include an identity service and a data discovery service, and each landing zone includes a FHIR server and a cross-platform interface engine configured to: receive a data file from a participant data source for one or more members; call an endpoint in the identity service to register the one or more members based on one or more attributes in the data file that indicate demographics for the one or more members; receive unique identifiers for each member from the identity service; map the data file to a FHIR resource for the data file; store data corresponding to the data file in the FHIR server based on the FHIR resources; receive resource locators from the FHIR server for the stored data; and register the resource locators with the data discovery service.

In some implementations, the one or more collaboration services include an identity service, a data discovery service, and a workflow authorization service; the one or more distributed ledger services includes a blockchain service; a first landing zone includes a solution that includes a first application configured to: call a first endpoint in the identity service to search for a member; receive a unique identifier for the member from the identity service; call a second endpoint in the data discovery service using the unique identifier; receive one or more FHIR resource locators for the member from the data discovery service; transmit a request for the FHIR resource or for a service to be performed on the FHIR resources to a second landing zone based on the one or more FHIR resource locators; and receive FHIR resource data or the result of executing the transaction request on the FHIR resource data for the member from the second landing zone; and the second landing zone includes a second FHIR server that is configured to: receive the request from the first landing zone; transmit an authorization request to the workflow authorization service for the received request; receive a response to the authorization request from the workflow authorization service; and send the FHIR resource data or the result of executing the transaction request on the FHIR resource data from the second FHIR server to the first landing zone.

In some implementations, the one or more applications are reconfigurable based on constraints of the health utility platform.

In another aspect, a method is provided for configuring and/or managing a health utility network. The method includes: providing a network of (i) a plurality of virtual machines, and (ii) one or more blockchains, each with one or more blockchain nodes for storing data, such as for pinning transaction hashes and storing network or other configuration data, and for running smart contracts; providing a data highway for accessing data stored in the network by participants who have a valid HIPAA reason to consume the data, wherein the participants are communicatively connected to the network via the plurality of virtual machines; and providing one or more data channels for defining and restricting access, via the data highway, to protected health information (PHI) based on specific use cases. In some implementations, the method further includes: receiving a transaction from a first virtual machine of the plurality of virtual machines, wherein the transaction corresponds to a member of a participant; searching for a member identifier and associated metadata for the member corresponding to the transaction; authorizing the transaction to transmit using the data highway; and transmitting data corresponding to the transaction to a second virtual machine of the plurality of virtual machines, based on the authorization. In some implementations, the method further includes recording a hash of the transaction on one of the one or more blockchain services. In some implementations, each virtual machine includes respective compute and storage environments. In some implementations, each virtual machine is configured to execute one or more decentralized applications sourced from a managed solution repository. In some implementations, one or more participants subscribe to the one or more decentralized applications, the one or more decentralized applications are enabled in each subscriber's landing zone, and a decentralized application is able to communicate directly with a similar instance of itself in any other landing zone. In some implementations, a first set of decentralized applications of the one or more decentralized applications provides one or more services to a second set of decentralized applications of the one or more decentralized applications. In some implementations, the one or more decentralized applications in a landing zone share data using a FHIR Server or other database tables in the landing zone. In some implementations, each virtual machine is configured to store data in a common format with common access means.

In another aspect, a method is provided for using a health utility network. The method includes: obtaining a member identifier for a member, by a first landing zone of a plurality of landing zones. Each landing zone includes respective compute and storage environments and is communicatively coupled to other landing zones via a network; searching the network for data for the member using the member identifier to obtain identifiers corresponding to one or more landing zones that have the data; selecting a second landing zone from the one or more landing zones; transmitting a request to the second landing zone for requesting transactions to be executed on the data local to each landing zone thereby causing the second landing zone to (i) authenticate and authorize the request using identity and access management and a workflow authorization server, and (ii) transmit the data or the results on transacting on the local data to the first landing zone; and receiving the data or transaction results from the second landing zone. In some implementations, the authentication and/or authorization uses ledger identities. In some implementations, transmitting the request to the second landing zone further causes the second landing zone to cause a distributed ledger service to pin a hash of the request on a blockchain using cryptographic hashes to create an immutable audit trail.

According to some implementations, an electronic device includes one or more processors, memory, and one or more programs stored in the memory. In some implementations, the electronic device includes a display. The programs are configured for execution on the one or more processors and are configured to perform one or more methods when the program is activated.

Both the foregoing general description and the following detailed description are exemplary and explanatory, and are intended to provide further explanation of the invention as claimed.

BRIEF DESCRIPTION OF THE DRAWINGS

For a better understanding of the various described implementations, reference should be made to the Description of Implementations below, in conjunction with the following drawings in which like reference numerals refer to corresponding parts throughout the figures.

Like reference numerals refer to corresponding parts throughout the several views of the drawings.

DESCRIPTION OF IMPLEMENTATIONS

Figure 1A:
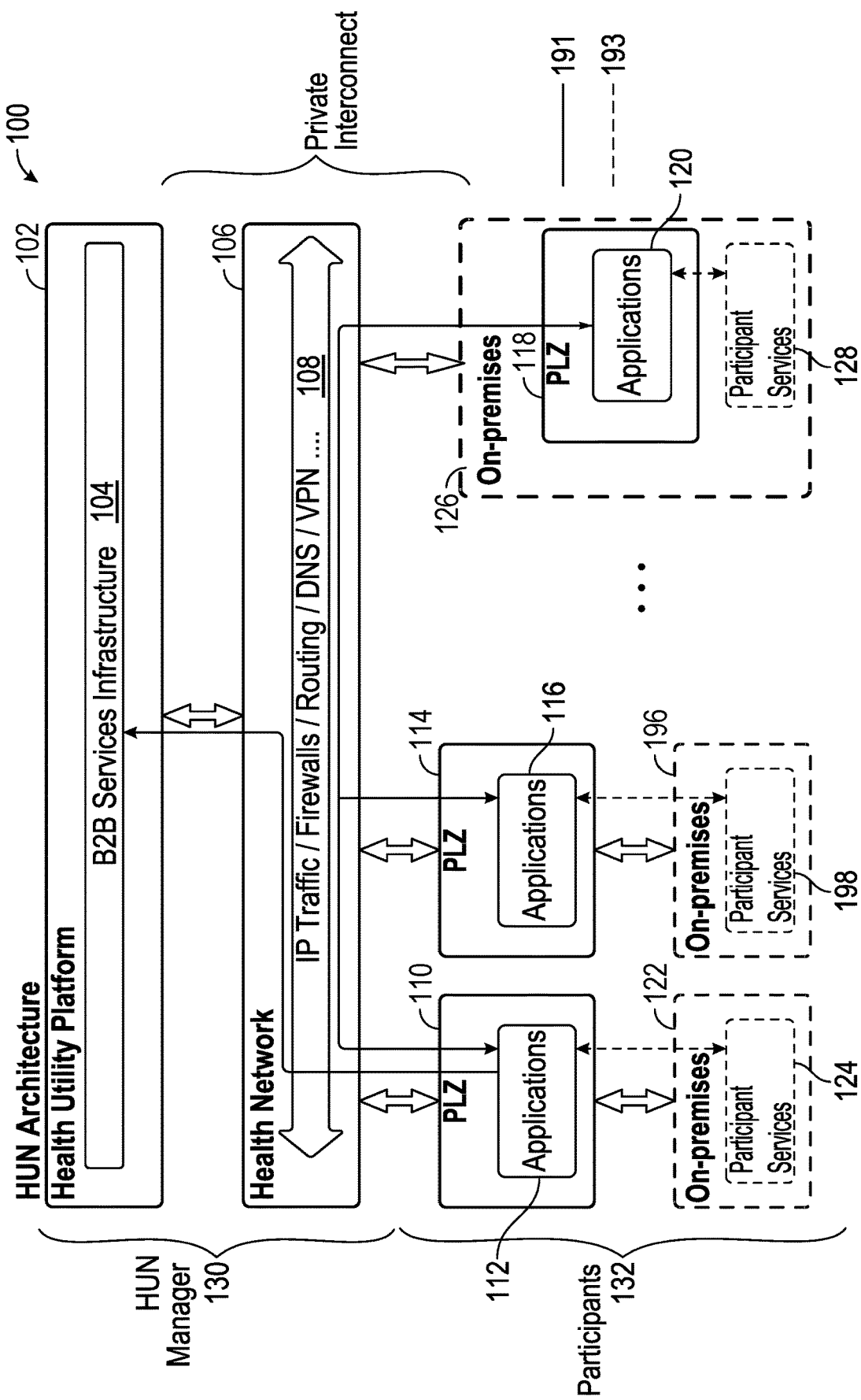
FIG. 1A is a block diagram of a multi-layer architecture and infrastructure for an example health utility network, according to some implementations.

FIG. 1A is a block diagram of a multi-layer architecture and infrastructure for a health utility network (HUN) 100, according to some implementations.

In the following description, participants 132 generally refer to providers and payers (sometimes referred to as tenants). In some implementations, the health utility network 100 includes a whole eco-system comprising a health utility platform (HUP) 102, a health network 106, landing zones (sometimes referred to as participant landing zones (PLZs), e.g., PLZ 110, PLZ 114, PLZ 118), and/or any network connects. In some implementations, the health utility platform 102 includes the infrastructure that hosts HUN network and collaboration services.

The HUN 100 architecture or design may fulfill several high-level requirements. The HUN 100 may provide a siloed multi-tenant environment to all HUN Participants. Participants have a fully isolated infrastructure footprint (a landing zone) which they have the option to fully control and manage themselves or have it managed by a central entity. The HUN 100 may provide a private and secure network interconnect (that can be expanded at a national level) which ensures connectivity between participants and business-to-business (B2B) services and systems in the HUN network. Access to the private network may be controlled and managed by a governing entity. Participants may be granted access to the HUN network and at the same time they may have the controls that allows them to isolate their landing zone (LZ) from the rest of the network if they opt to do so (disconnect from network). Communications or data transfers may be made only over the secure and private network provided by HUN and communication may not be permitted over public networks (e.g., Internet traffic may be restricted). Further, to ensure maximum levels of security, the in-network communication at application level may be limited only to permitted secure protocols, such as transport layer security/secure sockets layer (TLS/SSL), mutual TLS, and secure shell/secure file transfer protocol (SSH/SFTP). A network governing entity may control and impose these standards in order to ensure security and data isolation for participant-to-participant communication. The HUN architecture may allow a participant to connect to their on-premises infrastructure and services without exposing the on-premises infrastructure to the rest of the HUN network. A PLZ may allow for a downstream site-to-site private connection which may link the participant on-premises systems with the applications and services running in its landing zone.

The HUN 100 is an ecosystem of solution users, solution providers, innovators and accelerator entities that collaborate in a private and secure environment—a national "private healthcare Internet". Participant types may include solution user (participant), solution provider, or network accelerator. Solution users may include payers, providers and employers, pharmacy benefit managers (PBMs) or pharmacies, and life sciences. Solution users may include consumers/users of a solution or application available in the HUN applications marketplace without integrating ecosystem entities interested in executing HUN solutions. They directly benefit from the solution or integrate results with other non-HUN solutions. Solution providers may include developers, Health Information Exchanges (HIEs), and/or other networks. This includes software developers who are interested in developing Blockchain, non-Blockchain and mixed applications using common HUN services and utilities. A solution provider creates solutions and applications deployed in the HUN platform, and can be an independent software vendor (ISV) operator or enabler and reseller of solutions. Network accelerator may include data providers, clearinghouses and social services entities. A network participant may decide to play roles under multiple types. Network accelerator may include entities who provide data or analytical services that could be beneficial to the execution of HUN solutions (data or service providers); connectivity providers (network connectors) that can interconnect participants with the HUN over secure channels and/or facilitate connectivity between other participants.

Referring back to FIG. 1A, the HUN 100 includes the HUP 102, the health network 106 and the PLZs, according to some implementations. The HUP 102 may include infrastructure, systems and services that host and provide the B2B services which are consumed by the participants. The HUP 102 may include one or more applications (sometimes called solutions) to which participants may subscribe and have installed in their landing zone. This platform may be centrally controlled and managed. The health network 106 may include the network that will connect the participants in the HUN ecosystem. The health network 106 may provide secure and private connectivity between HUP and participants and between participants over a standard internet protocol (IP) layer. Conceptually this network may be thought of as a "private healthcare Internet" that provides private and secure traffic between the HUN entities. At an organizational level, this network may be centrally controlled and/or managed.

The participant landing zone(s) (sometimes referred to as PLZs) is a turn-key infrastructure solution that may be provided to the participants as a service. This may allow a new participant to establish connectivity with the rest of the HUN and may have an environment that allows them to subscribe and have deployed applications quickly and with minimal effort. Solution developers that create applications for subscription by participants can depend on the subscriber's deployment environment being configured identically with a common technology stack, minimizing installation and integration challenges. The PLZs may be either fully controlled by a participant (owner) or they may be centrally managed (managed PLZ). A PLZ may be a complete, production-ready deployment which provides a DevOps-style management and deployment environments, and which is HITRUST and SOC certified. Additionally, a PLZ may offer connectivity into the HUN network and (if desired) connectivity with the participants' on-premises systems and/or services using a private site-to-site connection (e.g., virtual private network or VPN, multi-protocol label switching or MPLS, etc.).

FIG. 1A shows a high-level organization of and communication channels in the HUN 100 system, according to some implementations. The figure also shows boundaries for infrastructure and the responsibility and control domains between a HUN manager 130 and the participants 132. In some implementations, there may be a demarcation between the HUP 102 and PLZs and between the PLZs in terms of one or more of the following:

infrastructure—no entity shares any resources (storage, compute, network etc.) directly with another entity;
  data—data transfers may be made via services over the private health network 106 that may include a backbone interconnect; no entity in HUN or PLZ may provide direct access to data stores; data transfers may be authorized and recorded (such as by pinning a hash of transactions on a ledger) by the B2B services that HUN provides. A data transfer may take place only after the two parties agree upon and the systems may determine that the two parties are authorized to the transfer (similar to an SSL handshake and authorization). Data flow or data transfer may include transaction negotiation, authorization and personally identifiable information (PII)/protected health information (PHI) data transfer;

management and security—the HUP 102, the health network 106 and the PLZs each may have their own management domain (root level) in terms of security and infrastructure. The HUN manager 130 may control the HUP and health network 106 while each participant 132 has control and is responsible for its own LZ;

network—the health network 106 provides the interconnect, access and security controls required to safely connect all entities in HUN. Participants may connect into the network using a secure site-to-site channel, such as MPLS, VPN and/or network peering. A participant 132 may have their PLZ connected to their private on-premises infrastructure using similar site-to-site secure channels. The system 100 may not allow any of the participants 132 to communicate over public networks. Each member 132 may have the option and controls that allows them to disconnect/isolate from HUN (e.g., from the health network 106) and the HUN manager 130 may control and isolate any of the participants 132 if necessary (e.g., using circuit-breakers at both ends of the participant-to-HUP communication channel).

In FIG. 1A, lines 191 and dashed lines 193 show communications or data transfers, according to some implementations. The applications may exchange data with the B2B services infrastructure 104. The applications and/or application-level protocols may also exchange data with other applications. Participant source systems 122 may exchange data with the applications. The types of protocols allowed for application communication is imposed strictly by the firewalls that are configured in the health network 106 in order to ensure complete data isolation of transfers between HUN participants. The participants may be able to access only data that is addressed to them and they cannot access data transfers in which they are not an intended party.

Some implementations may map the model shown in FIG. 1A into concrete components hosted in on-demand cloud computing platforms and APIs and/or web services (e.g., Amazon Web Services (AWS)). FIG. 1A shows a high-level view of the architecture of the HUN 100. Each of the HUN components may have their own internal organizational hierarchy. In a simplified view, the hierarchy may be seen in two tiers, one which is HUN-managed (e.g., by the HUN manager 130) and another tier which is managed by the participant 132. The HUP 102 and the health network 106 may be under the same organization account (e.g., a root cloud account) since they are managed by a single entity (the HUN manager 130). Each PLZ may have an associated root account owned by a participant. The relation between root accounts, PLZ and participants may be a 1-to-1-to-1 relationship (e.g., a participant has a single root account and a single landing zone). In some implementations, the root may be the core HUN management account and may be owned by the HUN manager 130. This account may be used as the parent for the HUP 102 and the health network 106 accounts. The HUP 102 may include one or more health utility blockchains (HUB). Some blockchains may have their nodes directly included in the landing zones. A separate management account may be used for the blockchain infrastructure(s) (or the HUP 102). Some implementations may replicate the same structure for each PLZ in order to provide a common deployment environment. In some implementations, the HUB organizational model may evolve towards a more complex organizational model as the HUN 100 matures (e.g., more participants are added to the network, more data is exchanged). The health network 106 may use a separate management account. Some implementations may provide participants with a management account. Users of these accounts may perform administrative tasks for managed PLZs (e.g., using inter-account permissions).

In some implementations, the health utility platform 102 includes infrastructure that hosts B2B service that are provided to HUN participants. The HUP 102 may be administered and managed by the HUN manager 130. The HUP deployment model may be similar to the PLZ. The health network 106 may be based on cloud traffic gateways (e.g., AWS Traffic Gateway).

In some implementations, the health network 106 is the network layer which implements and provides a secure and private IP layer connectivity between the HUN manager 130 provided B2B services infrastructure and participants and also the participant-to-participant connectivity channels. The health network 106 may be extensible for using various connectivity models, such as MPLS/leased lines, VPN, network peering or any other secure connection types. In some implementations, the health network 106 may use a cloud-based interconnect (e.g., AWS PrivateLink) as platform or a similar interconnect platform. The network may be isolated as a sub-account of a HUN root account which deploys a single virtual private cloud (VPC) which manages networking resources that ensure HUN connectivity between the B2B services infrastructure 104 and the participants, and between participants. This may include sub-networks, firewalls, routers, DNS services, load balancers, VPN and NAT gateways. In some implementations, the health network 106 may include subnet spanning between at least three availability zones (sometimes referred to as backbone network). The network may provide required bandwidth to accommodate traffic between the HUN participants. The health network 106 may be firewalled, may not allow any public egress or ingress connectivity, may permit traffic only between HUN participants, may allow only application layer protocols (e.g., DNS, HTTPS, SSH, secure copy SCP, or similar protocols). The use of secure protocols may ensure that traffic between participants in the health network 106 is private (e.g. a participant cannot see the data transferred between other participants). The health network 106 may include internal-only routing; in other words, the health network 106 may not provide any external/off-network traffic. Some implementations may include internal DNS service for the health network 106 participants. The health network 106 may implement a DNS naming model where each participant is assigned a unique "root member-domain" in the health network 106 that is managed by the health network 106 or the HUN manager 130. Some implementations may include sub-domain management by the participants. If a participant chooses to use sub-domains that are self-managed the PLZ may run a second level DNS resolver that allows the member to expose their host names on the health network 106. In some implementations, managed names may be extended to a distributed model across PLZs, VPNs and/or across clouds. Private connections for HUN participants may be provided using network peering and network address translation (NAT) with HUB or with a PLZ if necessary and/or VPN gateways and NAT translation with PLZs so the participants can use their own IP address ranges in their PLZ without interfering with the health network 106 IP address ranges.

As described above, a PLZ is a turn-key infrastructure solution which may be provided by the HUN 100 for a participant in the HUN network. The PLZ infrastructure model may be provided as a service that allows participants to quickly bring up a HUN-connected environment or HITRUST certified environment in which they can subscribe to HUN-certified solutions, applications and services. The PLZ may be owned by a participant and the participant may allow the PLZ to connect to the HUN B2B network backbone. The PLZ may also provide all resources necessary for solution developers to develop applications that interact with the B2B services that HUN offers and submit their applications for certification followed by subscription by other participants.

In some implementations, there may be various types of PLZs. A participant may own or have its own PLZ deployment. The participant may be provided an option to either self-manage the system or have the system managed by the HUN manager 130. A self-managed PLZ may have the participant control and manage the infrastructure and applications themselves. With managed PLZs, a participant may delegate the infrastructure and application management to the HUN manager 130.

According to some implementations, for PLZs, the organization model may include a PLZ having a single managing organization or root account owned by a participant, environments may be isolated at (sub)account and VPC level, two categories of sub-account or environments cross functional and deployment/applications, and implement a HITRUST security model. Regardless of the model used, self-managed or the HUN manager 130-managed, infrastructure resources associated with a PLZ may be under a single participant level root account or organization. This means that a participant has full control over its own PLZ. In case of the HUN manager 130 managed PLZs, the organization model may use cross-account permissions that permit the HUN manager 130 to manage and administer the PLZ on behalf of the participant without (or at least with limited and audited) access to participant's data that may be stored in the participant's PLZ.

In some implementations, environments are isolated from each other. The PLZ may implement a certified zero-trust security model. In order to achieve zero-trust, the isolation model used by the PLZ to separate resources and control access to resources between the deployment environments may be based on account level isolation. Resources used by an environment may be under a single account or project. In some implementations, the entire PLZ architecture and infrastructure model is HITRUST certified. For full zero-trust/HITRUST, environments in a landing zone may provide data transfer isolation (no unauthorized data transfers between environments), network level isolation (e.g., separate VPC for each environment protected by firewalls), and/or centralized security management/identity access management (IAM) with full audit trails. A landing zone may provide a set of four environments that are intended to provide the infrastructure for a classic DevOps deployment pipeline: DEV, TEST, STAGING and PROD. The deployment pipeline may be used by participants that only subscribe to solutions that integrate with their on-premises applications as well as participants that develop applications for subscription by other participants. Additionally, a PLZ may have three separate environments that are used to provide common services that are specific to a participant's organization: SEC, SHARED and LOG (see detailed description below). Like the deploy environments, these are also using account level isolation. Conceptually, the environments provided in a PLZ may be segregated into four deployment/applications environments: DEV, TEST, STAGING and PROD, and cross functional environments: SEC (SECURITY), SHARED and LOG. A root account may be configured for the main participant organization level management account (owned by participants). Cross functional environments may include a SEC account which may be used only for IAM users and permissions, security policies management, monitoring and audit reporting. If the participant uses an external federated identity provider, such as active directory service (ADS), Lightweight Directory Access Protocol (LDAP), etc., this account may be used as the integration point. The SEC account may also own the storage (e.g., S3 buckets) which is collected for all IAM operations. This account may not contain any resources except those required for IAM integration and audit using a service such as CloudTrail. In some implementations, by default, the only resource used may be a cloud storage S3 bucket for long term storage of the audit trails/logs. IAM audit trail logs may be accessible only to the members of the SEC group and they may not be shared with any of the other environments (e.g., LOGS). LOGS may include data access logs. If data access logs need to be stored by a participant, as required by HIPAA/HITRUST compliance, a secondary "data access logs" storage bucket may be created in the SEC account. This bucket may contain only data access audit logs. A LOG account may be used to aggregate logging data from applications and systems running in the deploy environments for monitoring and reporting purposes. The infrastructure may include long term storage buckets (S3 buckets) and/or tools used for logs access, search and reporting (e.g., Splunk). One important exception is the fact that security logs are not stored in this account (see SEC environment). A SHARED environment may be used for all shared infrastructure components and applications. Some implementations include an endpoint for OpenVPN or other site-to-site connectivity method towards the participant source systems 122. A PLZ may offer OpenVPN for on-premises access. Other functionality that may be hosted here are version control servers (e.g., git servers, Gitlab, etc.), jobs/CI pipeline management servers such as Jenkins, elastic container registry (ECR) registries, etc. (e.g., any service that fulfills a PLZ wide function may be hosted here). Deployment environments may include production ready/DevOps zero-trust multi-stage environments. Each environment that requires network resources may have its own VPC and firewall. Each environment may span multiple availability zones (e.g., 4 zones). PLZs may use production ready infrastructure model optimized DevOps development pipelines that provide a classic/standard 4-tier multi-stage deployment environment—DEV, TEST, STAGING, PROD which a participant can use to develop and deploy own applications/solutions or which are used by the HUN Manager to stage and deploy applications subscribed to by the participant. A DEV environment may be the first stage in a deployment pipeline and may act as a sandbox where developers can deploy their applications as often as required and where unit testing is done. In terms of Continuous Integration/Continuous Delivery (CI/CD), a developer may be allowed to manually deploy applications in this environment, but the recommended path is to have all deployments use a CI/CD pipeline to deploy even in DEV. The DEV environment may run a container cluster (e.g., Amazon Elastic Kubernetes Service (EKS)) and may provide a way for developers to easily access and configure the containers/ docker images in which an application is deployed (e.g., this environment is where configuration is permitted). The DEV environment application instances need not be stable or reliable. The DEV environment may not contain any sensitive or production data—especially if this data is PHI/PII or HIPAA related information. A TEST environment may allow humans (and automated testers) to exercise and validate functionality of new or changed code. Also, the test environment is considered as being the place where integration testing is done. Deployment to TEST may be possible only via a CI/CD pipeline, developers may not be allowed to make any direct changes to the environment and any deployment must follow (depend on) a successful deploy of the same code version in DEV (only valid promoted builds may be deployed to TEST). The environment changes may be published via CI/CD pipelines only. The deployment of subscribed solutions may use a similar method.

In some implementations, the TEST environment does not provide any development tools, but it may provide debugging and tracing and automated test tools if necessary. In terms of data, the test environment may not contain any PROD data, using simulated or synthetic data instead. STAGING (pre-production) is an environment where the final validation and user acceptance tests may take place. A successfully tested release can be promoted to STAGING from TEST using the same CI/CD pipeline dependency approach described for transition from DEV to TEST. In STAGING, there may be sensitive information, depending on the member's policies/decision. A separate environment/ stage may be used where the HUN manager 130 does code validation and application certification. A PROD production environment also known as live environment, is the environment where users may interact with applications. This environment may not contain any development tools. Deployments and environment changes to PROD are made strictly via a CI/CD pipeline. IAM configuration may be standard compliant starting point for IAM configuration. Single "admin" user with full IAM management rights may include default roles that control IAM operations and audit log access, and may act as an integration point with federated authentication providers. A default IAM configuration may be deployed in a PLZ that provides a compliant starting point for a participant to customize and extend the standard model. A participant may extend their IAM configuration to include more users, roles and customize it to fit their organization-specific structure and requirements.

In some implementations, for users, initially, there may be only one user that has full IAM and security management control for the entire PLZ. The admin user may be configured and permissioned to manage this account and may perform all IAM related management tasks. Further extension/grant access to other users is left to the participant's latitude.

Roles for users may include IAM_ADMIN (users having this role are allowed to perform changes in the IAM; they have read write (RW) access and can manage roles and users); IAM AUDIT (grants read-only (RO) access to the IAM data for users or applications that perform audit and reporting functions); SEC_LOG_RW role which is allowed to modify and write the S3 audit storage bucket (this may be given to an audit service, such as CloudTrail); SEC_LOG_RO role that is allowed only to read and query the audit logs and reports, such as CloudTrail logs and reports (for example a security monitoring tool may be assigned in this role); DATA_ACCESS_RW role assigned to applications and services that record data access (created only if data access logs are required); DATA_ACCESS_RO role assigned for users and applications that may perform reporting and audit of the data access logs (created only if data access logs are required).

In some implementations, for network, each deployment environment has its own VPC and isolated network segment. A VPC may be divided in sub-nets at availability zone level and functional level. Ingress connections from public networks may not be permitted. For subnets, since each environment may be hosted in own account/VPC, this describes the subnets that are created for an environment across multiple availability zones. The secondary level of subnetting may be at a functional level—private subnets, public subnets, dedicated subnets (for example each application may have its own subnet). Given that an environment spans more than one availability zone (AZ), the number of actual subnets may be multiplied with the number of AZs that the environment spans (e.g., a maximum of 4). A PLZ may have the following subnets: hun_public—a 10.0.128.0/18 Class A subnet (16382 IP addresses) which is further split in 4×/20 class A subnets (4094 IP subnets). This subnet may host NAT gateways or NAT instances and application load balancers which are "connected" to the applications that are running in the shared ECS cluster/shared private subnet; shared_private—this may be the core subnet which hosts the bulk of the deployed applications. This may be a 10.0.0.0/17 subnet (32766 Ips) which can be split across 4 Azs using/19 subnets (8187 Ips); spare and dedicated private subnets may be provisioned depending on the Participant requirements and the type of applications that are deployed. These subnets may not be configured by default in a deployment but the management scripts that can provision such subnets may be available in an infrastructure-as-code tool, such as AWS Tower or Terraform.

In some implementations, applications deployed into a PLZ are containerized (such as by using Docker containers) that run either on an ECS cluster and/or a Kubernetes cluster which may span across PLZs in an environment. In order to ensure a zero-trust/HITRUST level isolation, deployment environments may not permit any unauthorized traffic between them; all subnets in an environment may also be protected by firewalls that contain all traffic within an environment and do not permit direct, unauthorized traffic between them.

In some implementations, each PLZ is connected upstream with the health network 106 and/or may provide an optional private downstream connection with the participant source systems 122. A PLZ may not provide any incoming connections from public networks/Internet (external ingress) but it may provide outgoing connections (external egress). The following connections may be replicated per deploy environment: connection between the PLZ and the health network 106 private connection may be using a cloud-based private connection (e.g., AWS Private Connect); connection between the PLZ and on-premise may use site-2-site connections tools, such as Open VPN.

Referring back to FIG. 1A, in some implementations, the health utility platform 102 comprises a software-as-a-service (SaaS) platform that includes a set of business-to-business (B2B) services, sometimes referred to as collaboration services, and ledger nodes that the HUN manager 130 hosts and provides to participants. The B2B services may include national-level servicing with multi-region deployments, high capacity and/or highly resilient deployments, synchronous REST web services, and/or asynchronous publishing/subscription model (e.g., Kafka). In an alternate implementation, one or more of the blockchains and nodes may be hosted directly within each PLZ.

In some implementations, the health network 106 includes a private network interconnect which provides access, routing and service discovery. The health utility platform 102 may host network services of the health network 106. The health network 106 may include internet protocol (IP) traffic, firewalls, routing, load balancing, DNS, VPN, or similar functionality, collectively labeled 108. A participant landing zone (PLZ) (e.g., PLZ 110, PLZ 114, PLZ 118) is an infrastructure that ensures connectivity for participants (e.g., providers and payers, sometimes referred to as tenants) to the health network 106 or the health utility platform 102 and runs applications (e.g., applications 112, 116, 120). The applications may be resource-consuming and/or provide services on the health network 106. The applications may be developed by solution providers and/or may be hosted in an application marketplace. Participant source systems 122 may provide or consume data or internal services (participant services or infrastructure 124) to the PLZ applications 112. Similarly, on-premises systems 196 may provide or consume data or internal services (participant services or infrastructure 198) to the PLZ applications 116, and on-premises systems 126 may provide or consume data or internal services (participant services or infrastructure 128) to the PLZ applications 120. The PLZs may be configured within an on-premises system. For example, in FIG. 1A, the PLZ 118 is configured within the on-premises system 126.

Figure 1B:
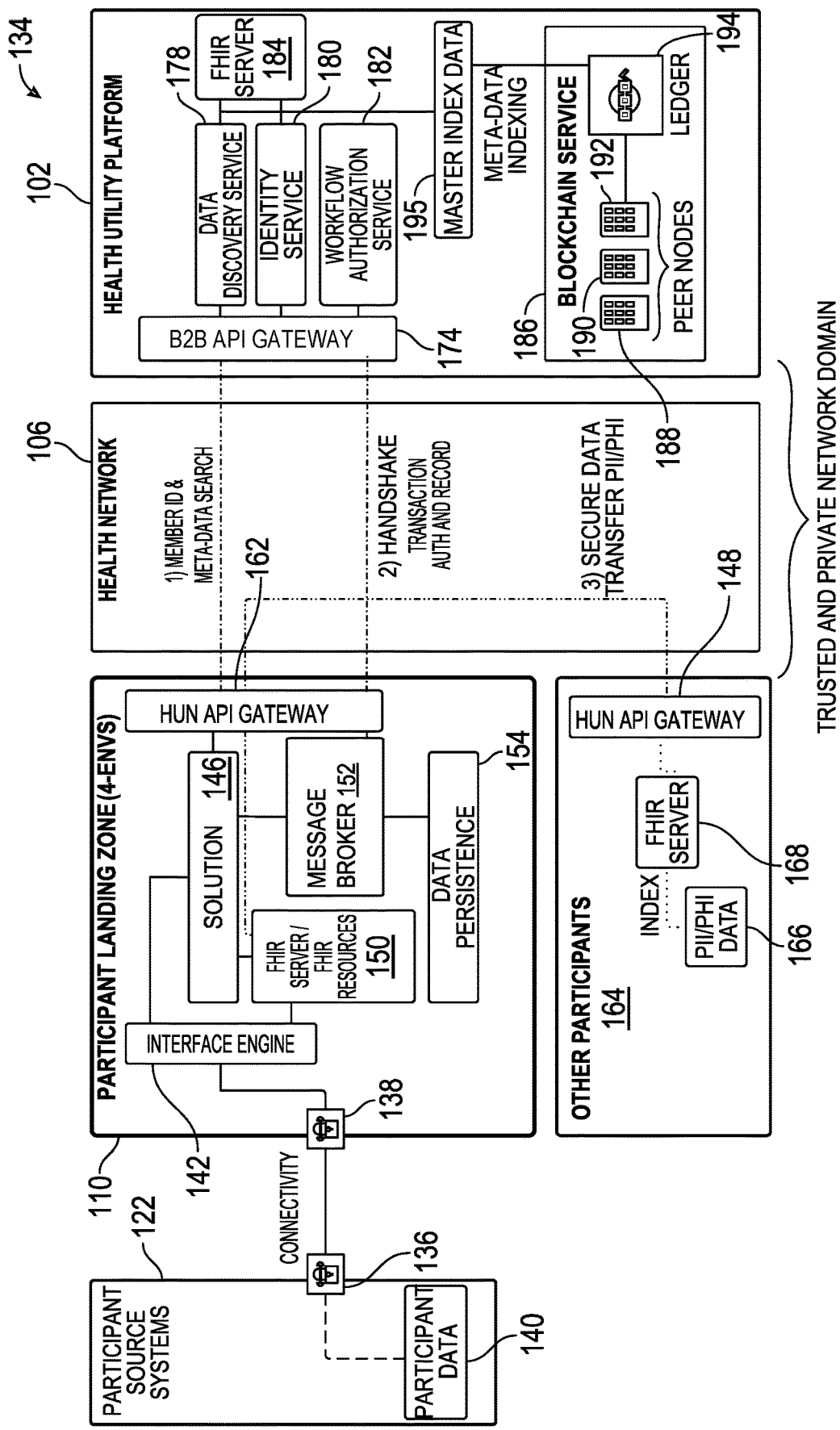
FIG. 1B is a block diagram of an example data flow architecture for the health utility network, according to some implementations.

FIG. 1B is a block diagram of an example data flow architecture 134 for the health utility network 100, according to some implementations. As described above, data flow in the HUN 100 may include transaction negotiation, authorization and/or PII/PHI data transfer. The participant source systems 122 may include participant data 140, and may be connected to, and configured to exchange services and data with, the PLZ 110 via connectivity 136 and 138.

In some implementations, the health utility platform 102 includes a software-as-a-service (SaaS) platform that provides B2B services for national-level servicing with multi-region deployments, may include high capacity and/or highly resilient deployments, and/or synchronous REST web services, and/or may add asynchronous publishing or subscription model (e.g., Kafka or custom resource subscription application). The health utility platform 102 may include a data discovery service 178 to search a master index data 195, locate/link data providers to a unique identifier usable for network search and to return the data location(s). The health utility platform 102 may include an identity service 180 (sometimes referred to as a member identity service 180) to match patient common data to unique identifier and to use a generic database or a FHIR server 184 for common patient data. The health utility platform 102 may include a workflow authorization service 182 for services registry, resources management, updates, traffic shaping and control, and participants identity integration with a ledger 194. The master index data 195 may be used to obtain meta-data indexing for accessing the ledger 194. The health utility platform 102 may include a blockchain service 186 (sometimes referred to as a blockchain-as-a-service (BaaS) platform) that may include a ledger network comprising one or more peer nodes (e.g., nodes 188, 190 and 192) and the ledger 194. The BaaS may be provided by HUN manager or by a third-party vendor, and may be customized, fully managed and/or hosted by the HUN manager 130. This may include ledgers of the type provided by Hyperledger Fabric, Hyperledger Besu (Ethereum) and Corda Each participant may be allocated nodes in the one or more ledger networks which may depend on the needs of the one or more solutions the participant subscribes. Network identity and keys may be provided to and owned by participant and signed by the HUN manager 130. For example, the HUN manager 130 may own the root certification authority (CA) of a public key infrastructure (PKI) and may manage identity for participants, ensuring secure network access control and governance. Dedicated high throughput and low latency interconnect may be provided to facilitate rapid consensus and block propagation, for reduced blockchain transaction time.

In some implementations, the PLZ 110 includes an interface engine 142 to connect to the gateway 138. The PLZ 110 may include one or more solutions 146. The solution 146 may interact with the health network via a HUN application programming interface (API) gateway 162. The solutions may request a search for a member's data in the network using the unique identifier described earlier, may initiate transactions (e.g., approval/handshake followed by data transfer), may provide integration and additional enriched data as necessary, and may be implemented by the HUN manager 130 and/or solution providers. The solution 146 may link the applications to the core HUN B2B services via a B2B API gateway of the HUP 102. The solution 146 may work in conjunction with the data discovery service 178. The solution 146 may provide a common abstraction or API used by participants to interact with the ledger 194 without the need to interact with the lower-level ledger-specific APIs. The PLZ 110 may include a message broker 152 (e.g., NATS or Apache Kafka). In some implementations, the message broker 152 includes modules for private messaging, broadcasting, data pinning to a ledger, publisher/subscribe services and/or token creation. The message broker 152 may provide a multi-party chain gateway which abstracts the ledger platform, and synchronizes with and tracks ledger transactions. The PLZ 110 may also include a Fast Healthcare Interoperability Resources (FHIR) server and associated FHIR resources 150 (sometimes referred to as FHIR server, e.g., IBM FHIR Server) for processing, validation, and storage of healthcare data. The FHIR server 150 may be the PII/PHI data provider for a participant's data (e.g., data may be stored in the local databases and shared using FHIR standards on network). The PII/PHI data may be transferred between two participants' FHIR servers. For example, FIG. 1B shows other participants 164 which may include PLZ 114 and PLZ 118 (see FIG. 1A). PII/PHI data may be transferred between the FHIR servers 150 and 168, via the HUN API gateway 162 and the HUN API gateway 148.

A PLZ may be thought of as a footprint and link for a participant to the HUN 100. The PLZ may include turn-key infrastructure and connectivity solution provided to a participant by the HUN manager 130, managed either by the HUN manager 130 and/or by the participant. In some implementations, the PLZ provides production ready DevOps deployment environment, may be zero-trust model/HITRUST certified, may be packaged and deployed as on-premises solution. Each participant may own one or more landing zones, which may be self-managed or the HUN manager 130 managed, may include network-level isolation (e.g., separate VPC for each environment protected by firewalls), may include data transfer isolation (no unauthorized data transfers between environments described below) and/or centralized security management/IAM with full audit trails. Private link(s) may be provided to connect to the health network 106/HUN and the participants' on-premises systems. In some implementations, the PLZ provides a set of 4 environments establishing the infrastructure for a classic DevOps deployment pipeline: DEV (for development), TEST, STAGING and PROD (for production). The PLZ may also have 3 separate cross-functional environments that are used to provide common services that are specific to a participant's organization: SEC (for security), SHARED and LOG. The PLZ may be delivered with pre-configured applications/services, such as client services, ledger connectivity, API and VPN gateways, development tools (e.g., full DevOps pipeline), logging and monitoring tools. For a zero-trust/HITRUST certified environment, which may include trust zone boundaries, each environment may be isolated in its own trust zone protected by a firewall (e.g., using access control lists (ACLs)). The private connection towards the participant on-premises may be made via a site-to-site VPN tunnel situated in the SHARED environment; further traffic may be routed to each deployment environment via the access gateway. Only DEV environment may allow direct SSH access over VPN. All other environments may use a bastion node that will permit SSH connections to the virtual machines (VMs) that are in the given environment. HTTPS/TLS traffic may be allowed to reach all environments so applications that run on PLZ may access on-premises services or vice-versa (not environment to environment see next rule). Routing rules may not allow traffic between environments (e.g., DEV traffic cannot reach PROD).

In some implementations, the PLZs are deployed using the following deployment model. Each environment may use isolation at account level with applications capable to use Kubernetes namespace-level isolation. DEV to PROD environments may run isolated Kubernetes clusters which may host all applications. Each environment may be individually connected to the health network 106 segment. Deployment of applications may be controlled via CI/CD pipelines. SHARED environment may be used for common services such as development tools, CI/CD, code repositories and hosts the on-premises VPN gateway. LOG account may centralize, manage and monitor application logs (with HIPAA compliant storage rules). SEC account may be used exclusively for IAM integration, security policies management, monitoring, audit, and reporting. Each deployment environment may run one or more Kubernetes clusters which may serve as the platform for all applications and services in a PLZ. The solution 146 may provide the interface to the HUN B2B and client API to interact with a message broker 152 (e.g., NATS or Apache Kafka). The FHIR server 150 may index and serve participant-owned PHI/PII data (not mandatory, may be hosted on-premises). The message broker 152 may act as the interface to one or more blockchain service and may provide connectivity and transaction tracking services for the solution 146, or may use a local database/index for transaction tracking. The PLZ may run two separate API gateways—one that is intended for participant's internal use and one which exposes services towards HUN. The solution 146 may be one or more solutions of the several available for subscription. All subscribed solutions may run in the same container or in parallel containers.

The PLZs may use the health network 106 for (i) member identifier and metadata search with the HUP 102, (ii) handshake with the blockchain service 186 (e.g., handshakes for transaction authorization and recordation), and (iii) connect to other participant FHIR servers. The health network 106 may be a private interconnect between HUN participants and the HUP 102.

In some implementations, the health network 106 includes infrastructure which provides the backbone interconnect between all HUN participants. The infrastructure may be secure, based on Cybersecurity & Infrastructure Security Agency (CISA)/Trusted Internet Connections (TIC) 3.0 federal network guidance and architecture with clearly demarcated trust zones (e.g., isolates participants in own trust zone). The infrastructure may be private and access into network may be managed by the HUN manager 130 (disconnect options to participant), may use internal DNS and routing, and data may not leave network except through authorized transactions. The infrastructure may be confidential and only encrypted (mTLS) traffic may be permitted on the network; only authorized parties can discern the contents of data in transit. The infrastructure may support managed traffic whereby observe, validate, and filter data connections to align with authorized activities and may include least privilege and default deny. The infrastructure may be scalable, may be at national level, enterprise level, multi-tenant on multiple cloud service providers, and/or national level network (e.g., Equinix, VZN, ATT etc.). The infrastructure may be resilient and resilient application and security services may be provided for continuous operation, future proofing as technology evolves.

Figure 4:
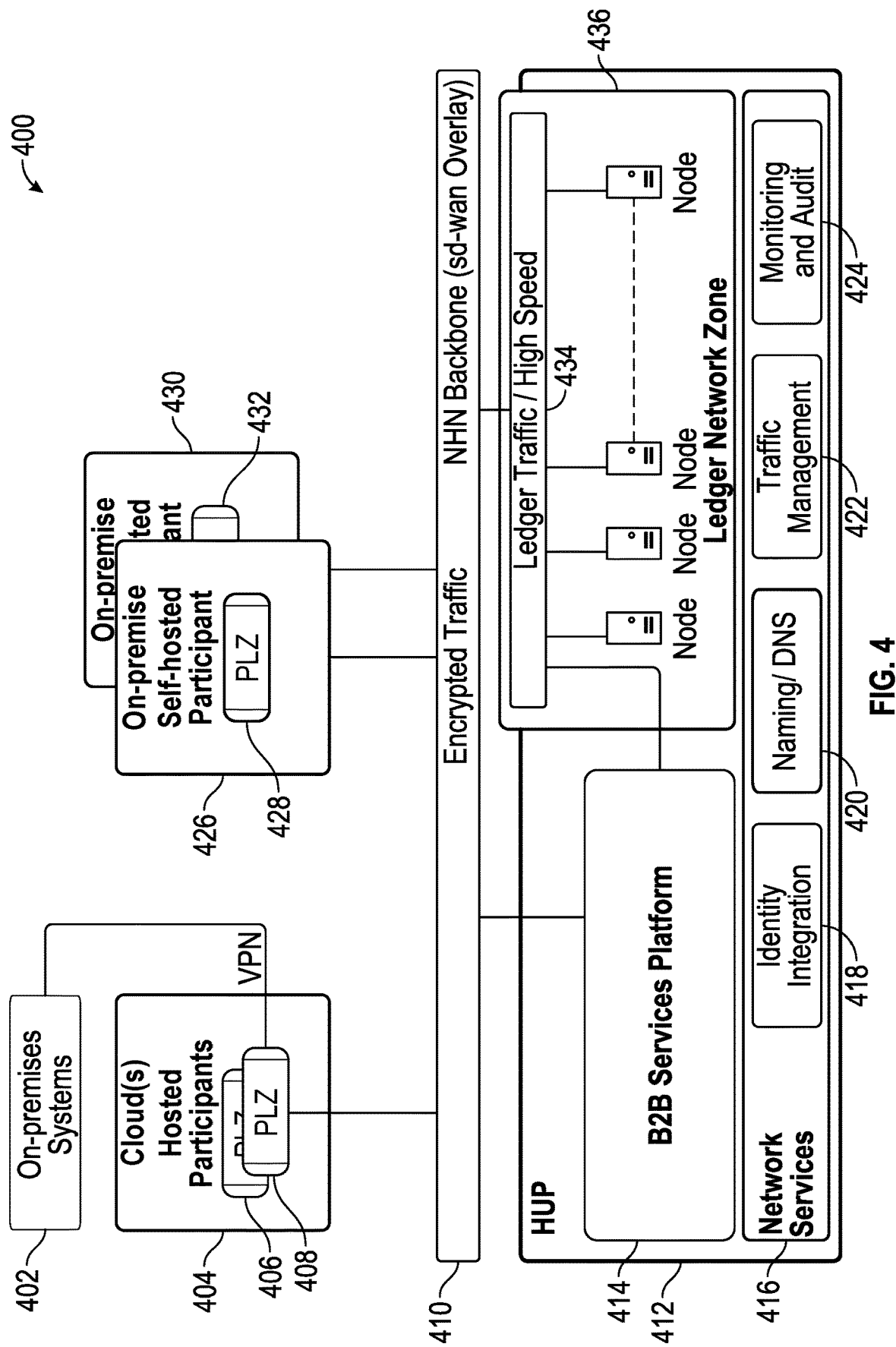
FIG. 4 shows example network aspects of a health utility network, according to some implementations.

FIG. 4 shows example network aspects 400 of the HUN 100, according to some implementations. In some implementations, the health network 106 is based on a software-defined wide area network (SD-WAN) 410 (sometimes called a national health network backbone) or a similar virtual WAN architecture model which may provide endpoint verification. The health network 106 may be able to use all connectivity mediums, overlay network service over one or more networks (e.g., Internet, WAN, classic MPLS, LTE, VPN-slice). The health network 106 may be multi-site and multi-cloud capable to service any connection type. The health network 106 may be an encrypted network whereby overlay traffic is encrypted and application protocols that are allowed on the network are controlled. Physical network access may be managed by the HUN manager 130, may use standard authentication, may be integrated with ledger identity, and/or may be outsourced to one or more cloud service vendors for the cloud components. Endpoint verification may unify participant's network access and authentication with the ledger identity. FIG. 4 shows on-premises systems 402 connected via a virtual private network (VPN) to cloud-hosted participants 404 which includes PLZs 406 and 408. The cloud-hosted participants 404 may be connected to the backbone 410 which carries encrypted traffic. The network may also include on-premise self-hosted participants 426 and 430, each of which may include a respective PLZ (e.g., PLZ 428 and PLZ 432). HUP 412 (e.g., the HUP 102) may include B2B services platform 414 (e.g., the B2B services infrastructure 104) which is connected to the backbone 410. The HUP 412 may also be connected to a ledger network zone 436 via a high-speed network 434. The ledger network zone 436 may include ledger nodes. The HUP 412 may also include network services, for identity integration 418, naming/domain name service (DNS) 420, traffic management 422 and/or monitoring and audit 424.

Figure 1C:
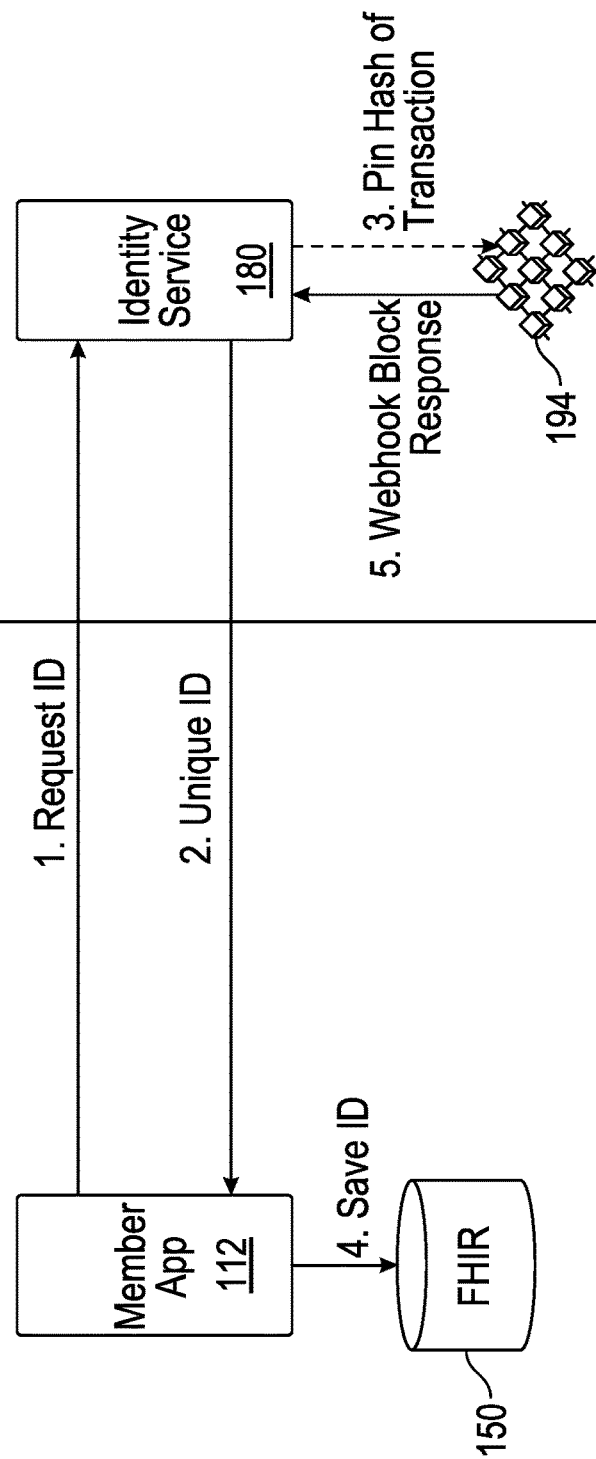
FIG. 1C shows a schematic diagram for transactions and data flow using multi-stage transactions with a health utility platform, according to some implementations.

Referring back to FIG. 1C, the figure shows a schematic diagram for example transactions and data flow 187 using multi-stage transactions with the HUP 102, according to some implementations. In some implementations, a member application 112 is connected to the identity service 180 and the FHIR 150. A member search function is incorporated into identity service 180. The member search function may be implemented using elastic search. The member identity service 180 may also be connected to a ledger 194. Synchronous flows are indicated by lines and asynchronous flow (between the member identity service 180 and the ledger 194) is indicated by a dashed line. For a search, a requesting party uses common patient identifiers to obtain a unique identifier and launches a search for it. For example, in FIG. 1C, the member application 112 posts (step 1) a request identifier for a patient to the identity service 180. The identity service 180 may return (step 2) the unique identifier to the member application 112. The member application 112 may save the unique identifier in the FHIR server 150. Returning to the search request, the identity service 180 may search the network for data using the unique identifier and may respond with the identifiers of the parties that have matching data (e.g., as links). The requesting party may select the parties from which it wants to receive data or to request a transaction be performed by the other party on their local copy of the data and return a result of the transaction. For a handshake with a data providing party, authentication between the participating parties may be performed using ledger identities, authorization and key negotiation or ledger managed key, and transaction may be pinned (step 3) on the ledger 194 using cryptographic hashes. The step 3 is an asynchronous step and the ledger 194 may respond with a block response (step 5) during the transaction or after the transaction is complete. For data transfer, data may be transferred directly between parties using the FHIR server 150, or may use a message broker between the two PLZs, transaction may be sealed (e.g., committed on chain), and the requester may then use the exchanged data. Ledger transactions do not contain PHI/PII data. The steps shown may be optional in some implementations, and the steps may be performed in a different order than the order shown in FIG. 1C, according to some implementations.

Figure 2A:
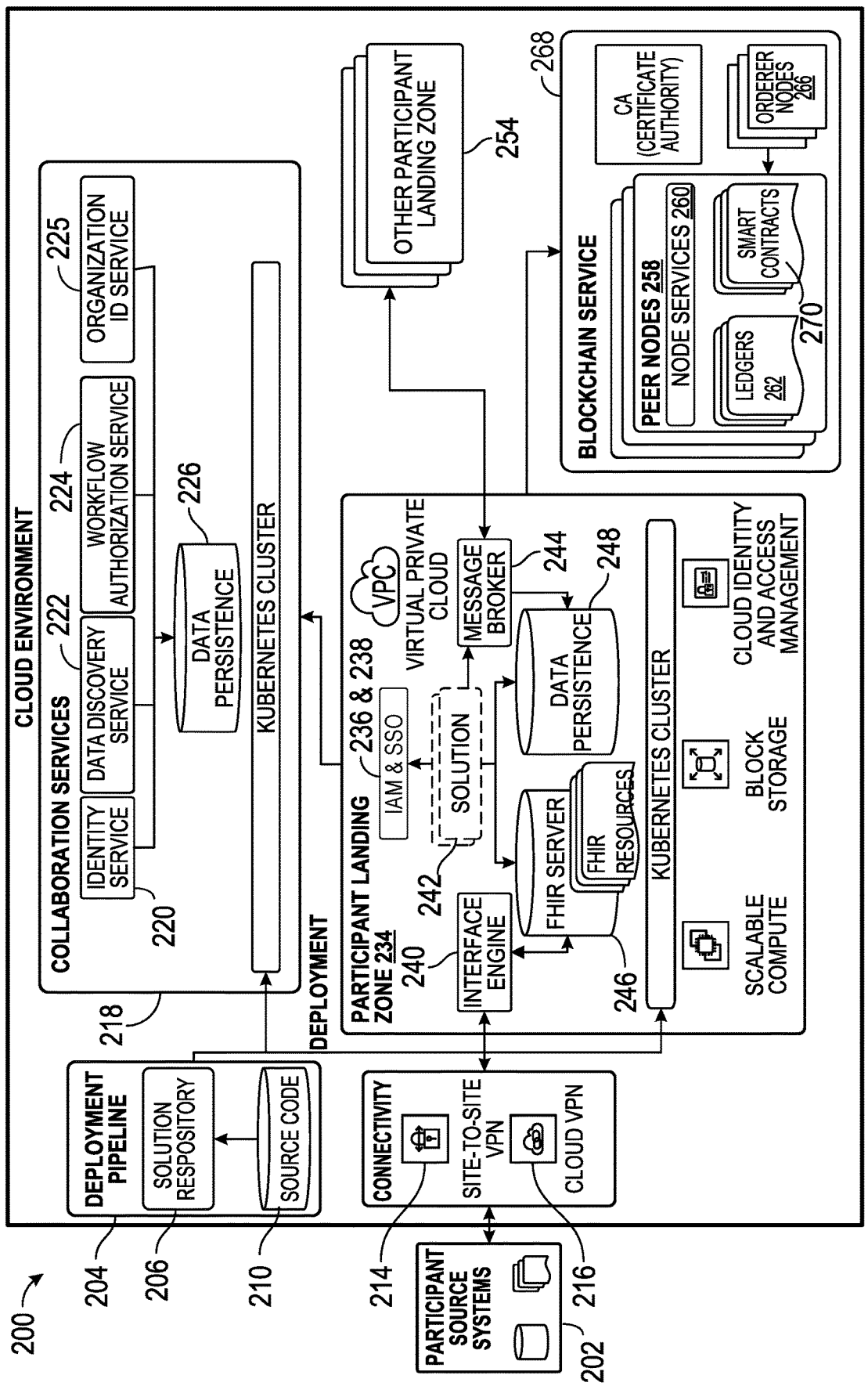
FIG. 2A is a block diagram of an example system architecture for the health utility network, according to some implementations.

FIG. 2A is a block diagram of an example system architecture 200 for the health utility network 100, according to some implementations.

As described above in reference to FIGS. 1A-1C, the HUN 100 (sometimes referred to as a system) may include a health utility platform (e.g., the HUP 102), a health network (e.g., the health network 106) communicatively coupled to the health utility platform, and a plurality of landing zones (e.g., the landing zones 110, 114 and 118) communicatively coupled to the health utility platform via the health network. Each landing zone is configured to run one or more applications for a participant (e.g., a provider, a payer). The one or more applications are configured to consume and process data and/or provide services on the health network. The health network may include a private network interconnect configured to provide access, routing, and service discovery.

Referring to FIG. 2A, in some implementations, the health utility platform is configured to execute one or more collaboration services (e.g., collaboration services 218) and one or more distributed ledger services (e.g., blockchain services 268). The one or more collaboration services and the one or more distributed ledger services may be configured to provide context or facilitate data exchanges between different landing zones of the plurality of landing zones.

In some implementations, each landing zone is configured in a virtual private cloud, as a set of components running in an environment for running containers. For example, FIG. 2A shows a participant landing zone 234 in a participant account in a virtual private cloud (VPC).

In some implementations, each landing zone 234 includes at least a cross-platform interface engine (e.g., interface engine 240, such as Mirth Connect, used in the healthcare industry that enables the management of information using bi-directional transformation and sending of many types of messages), a Health Level Seven (HL7) Fast Healthcare Interoperability Resources (FHIR) server (e.g., FHIR server 246), a data storage (e.g., data storage 248, sometimes referred to as data persistence, e.g., data persistence 154, which may be based on one or more database engines, such as POSTGRESQL, MONGODB), a lightweight web server (e.g., IAM 236, for HTTP traffic, proxy, reverse proxies, etc.), an authentication and authorization tool (e.g., SSO 238, for sign-on), and access to blockchain services (e.g., via message broker 244, for access to smart contracts). In some implementations, the interface engine 240 is included in the interface engine 142 (See FIG. 1B).

In some implementations, the one or more collaboration services (e.g., the collaboration service 218) include an identity service (e.g., an identity service 220, sometimes referred to as the identity service 180) configured to generate a unique identifier for each patient or health plan member ("member"), based on deterministic and/or probabilistic matching. Matching may improve as more data about a person is loaded into the system, and matching depends on quality of data. In some implementations, an external service may be used to conduct the match process.

In some implementations, the one or more collaboration services (e.g., the collaboration service 218) include a data discovery service (e.g., data discovery service 222) configured to provide a FHIR resource-based directory service (e.g., using a data storage 226, sometimes referred to as data persistence, such as POSTGRESQL) for identifying participants that have data corresponding to a member.

In some implementations, the one or more collaboration services (e.g., the collaboration service 218) include a workflow authorization service (e.g., workflow authorization service 224) configured to perform authorization based on a plurality of levels of granularity, including data source, resource type and requesting entity.

In some implementations, the one or more collaboration services (e.g., the collaboration services 218) include a workflow authorization service (e.g., workflow authorization service 224) configured to authorize access to a data highway for accessing data stored in the health network by participants who have a valid HIPAA reason, such as for coordination of care or for processing of claims and payments related to care.

In some implementations, the one or more collaboration services (e.g., the collaboration services 218) include an organization identity service (e.g., the organization identity service 225) configured to generate a unique identifier for each organization that is managed by the HUN Manager 130 and provides an organization lookup service to return routing details used to route a transaction to that organization's landing zone.

In some implementations, the one or more collaboration services (e.g., the collaboration services 218) are implemented using one or more RESTful APIs.

In some implementations, the one or more collaboration services (e.g., the collaboration services 218) are configured in a virtual private cloud, as a set of components running in an environment for running containers (similar to configuration of the landing zones) such as by using Docker or Kubernetes containers.

In some implementations, the one or more distributed ledger services are configured to run on one or more blockchain services (e.g., configurable blockchain platforms, such as Hyperledger Fabric or Hyperledger Besu). In some implementations, the blockchain service includes (i) a first one or more nodes (e.g., peer nodes 258) configured to store copies of a blockchain and perform chain code or smart contract execution and transaction validation and (ii) a second one or more nodes (e.g., orderer nodes 266, sometimes referred to as ordering nodes) configured to provide an ordering service which determines the ordering of blocks on the blockchain and enforces access controls to channels. In some blockchain implementations, a blockchain channel is implemented as a virtual blockchain where resources including transactions and smart contracts are private, only visible to participants that are part of the channel. The peer nodes may include node services 260, ledgers 262 and smart contracts 270. In some implementations, the one or more distributed ledger services are configured to run smart contracts, including a smart contract used to pin hashes of transactions for audit purposes.

In some implementations, each landing zone (e.g., participant landing zone 234) is configured as a virtual machine with identical tools deployed in automatically horizontally and vertically scalable compute and storage environments. In some implementations, each landing zone is configured such that compute nodes in the landing zones automatically increase in number to satisfy a surge in demand. While the tools provided by the HUN manager 130 may be identical, the environments may vary in size to accommodate the participant's needs, such as varying in storage size by the amount of data stored in the landing zone by the participant or vary in the size of the compute engine(s) available according to the needs of the one or more applications to which a participant has subscribed.

In some implementations, each landing zone (e.g., participant landing zone 234) is communicatively coupled to a respective on-premises system (e.g., the participant source systems 122) configured to provide and consume data and/or internal services.

In some implementations, each landing zone (e.g., participant landing zone 234) is configured to connect with a participant source system (e.g., participant source system 202) for a respective participant via a secure connection, such as a site-to-site VPN connection 214 or a private link connection 216. The participant source system may include any system that includes the ability to exchange data, such as by using an EHR (electronic health record) system, a database, a data feed, or a file exchange).

Some implementations include a CI/CD (continuous integration/continuous delivery) account (e.g., an account in a cloud instance) for developing applications or solutions. Some implementations include a deployment pipeline 204 that may include a source code repository 210 that may include solution source code and Helm charts (for Kubernetes applications), Argo CD or similar controller for continuously monitoring and delivering applications, and/or a docket registry (e.g., container repository 206). The source code repository 210 is for the files containing the "source code" while the solution repository 206 is for storing the compiled code and the files containing instructions for how to deploy and label the containers. The development pipeline 204 may be used for developing and/or deploying the one or more collaboration services 218 and/or the solutions 242.

Example Data Ingestion Sequence

As described above, in some implementations, the one or more collaboration services (e.g., the collaboration service 218) include an identity service (e.g., the identity service 220) and a data discovery service (e.g., data discovery service 222), and each landing zone (e.g., the participant landing zone 234) includes a FHIR server (e.g., the FHIR server 246) and a cross-platform interface engine (e.g., a Data Connect service, such as the interface engine 240).

Figure 2B:
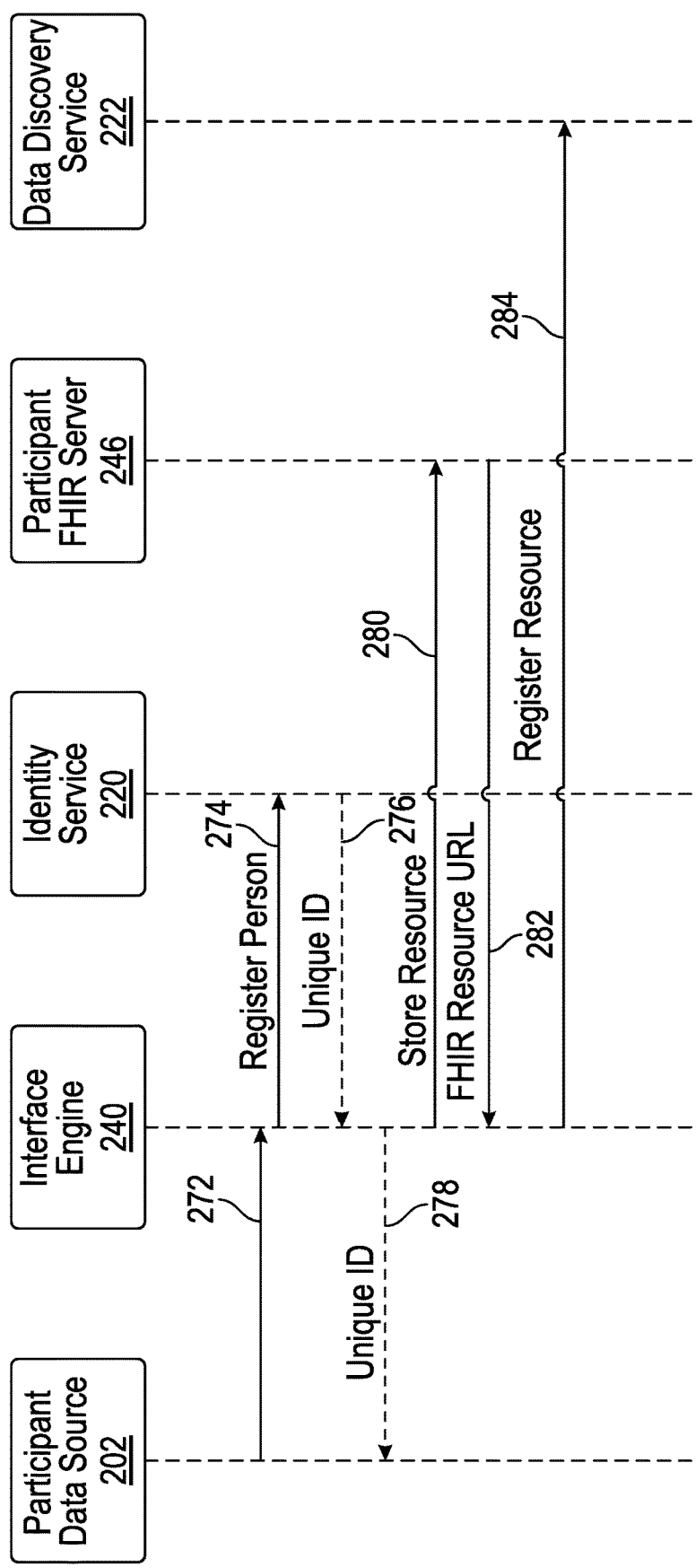
FIG. 2B shows a sequence diagram for an example data ingestion sequence, according to some implementations.

FIG. 2B shows a sequence diagram for an example data ingestion sequence 286, according to some implementations. In some implementations, the interface engine 240 is configured to: receive (272) a data file or transaction from a participant data source 202 for one or more members; call an endpoint in the identity service 220 to register (274) the one or more patients or members based on one or more attributes in the data file or transaction that indicate demographics for each member; receive (276) a unique identifier for each member from the identity service 220; map the data file to a FHIR resource for the data file (this step happens in the interface engine 240 and the step is not shown in FIG. 2B); store data (280) corresponding to the data file in the FHIR server 246 based on the FHIR resource; receive (282) a resource locator from the FHIR server 246 for the stored data; and register (284) the resource locator with the data discovery service. In some implementations, the interface engine 240 may transmit (278) the unique identifiers to the participant data source 202.

Example Application Service Interaction Sequence

As described above, in some implementations, the one or more collaboration services (e.g., the collaboration service 218) include an identity service (e.g., the identity service 220), a data discovery service (e.g., data discovery service 222) and a workflow authorization service (e.g., the workflow authorization service 224). The one or more distributed ledger services includes a blockchain service (e.g., the blockchain service 268). A first landing zone (e.g., the participant landing zone 234) may include a solution 242 that includes an application (e.g., application 293, for a participant A for the landing zone 234) installed in the landing zone. A second landing zone (e.g., a landing zone 254) for a participant B may include a second FHIR server 290 (not shown in FIG. 2A, similar to the FHIR server 246).

Figure 2C:
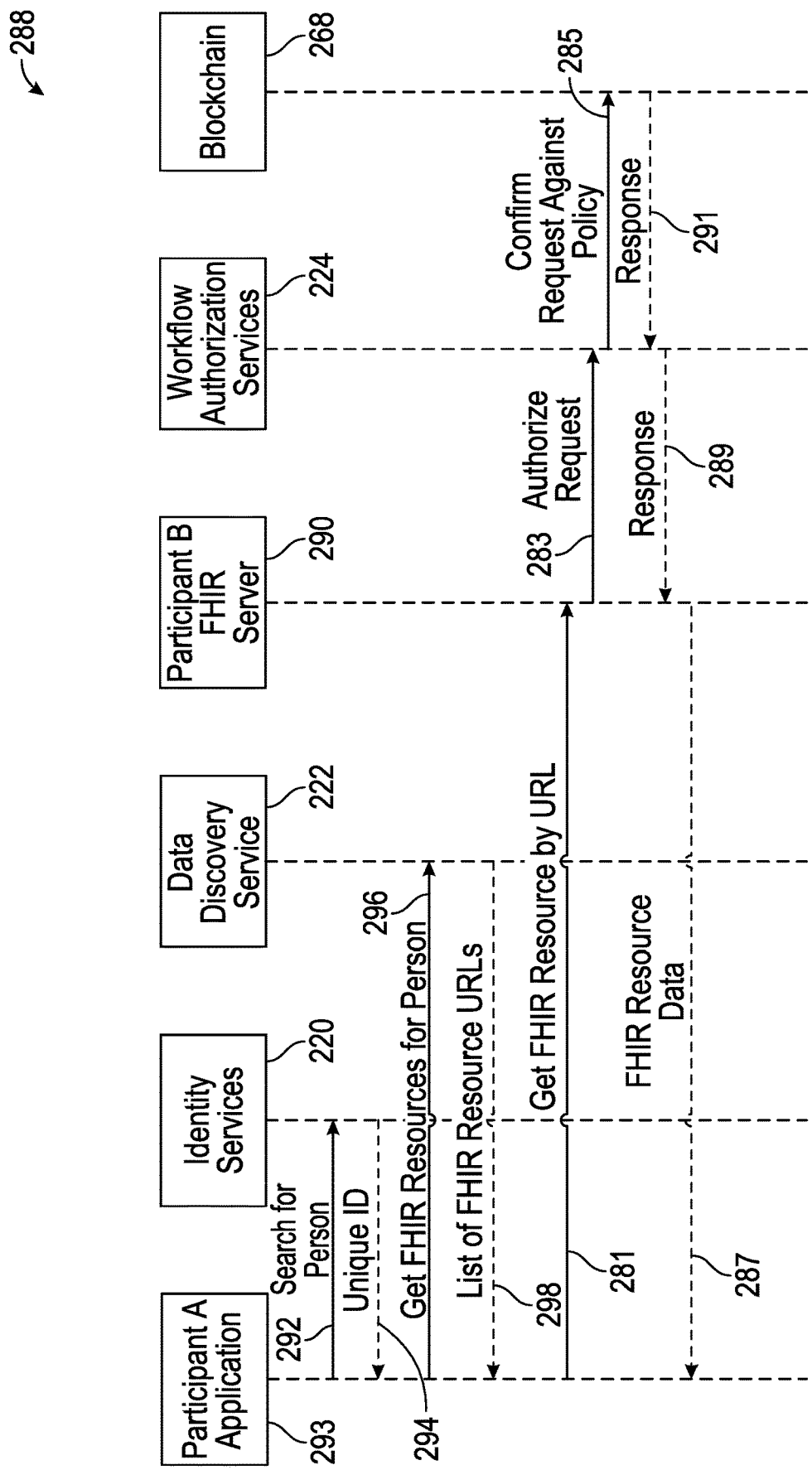
FIG. 2C shows a sequence diagram for an example application service interaction sequence, according to some implementations.

FIG. 2C shows a sequence diagram for an example application service interaction sequence 288, according to some implementations. In some implementations, the application 293 is configured to: call (292) a first endpoint in the identity service 220 to search for a member; receive (294) a unique identifier for the member from the identity service 220; call (296) a second endpoint in the data discovery service 222 using the unique identifier; receive (298) one or more FHIR resource locators for the member from the data discovery service 222; transmit (281) a request for the FHIR resource or for a transaction to be performed on the FHIR resource to a second landing zone (e.g., the second landing zone 254) based on the one or more FHIR resource locators; and receive (287) FHIR resource data or the result of executing the transaction request on the FHIR resource data for the member from the second landing zone 254. The second landing zone 254 includes the second FHIR server 290 that may be configured to: receive (281) the request from the first landing zone 234; transmit (283) an authorization request to the workflow authorization service 224 for the received request; receive (289) a response to the authorization request from the workflow authorization service 224; and send (287) the FHIR resource data or the result of executing the transaction request on the FHIR resource data from the second FHIR server to the application 293 running in the first landing zone 234. In response to the authorization request (283) from the second FHIR server 290, the workflow authorization services 224 transmits a confirm request against policy (285) to the blockchain 268 that answers with a response (291); the response (289) follows the response (291).

An example application service interaction sequence is, following data ingestion, suppose an application installed in a participant landing zone wants information on all coverages for a member registered in the system. As a first step, the application may search for a person with the identity service 220 and receive a unique identifier. In a second step, the application may call the data discovery service 222 to get FHIR resource locations for each coverage (e.g., 6 coverages) and receive the coverage location information as a list of FHIR resource URLs. The application may then contact a provider (e.g., participant B in FIG. 2C) corresponding to a FHIR resource URL. The FHIR server for that provider or participant may then get authorization to send that coverage and return authorized resource data back to the requesting participant (participant A in FIG. 2C). The sequence shown in FIG. 2C may occur simultaneously and/or asynchronously between any number of participants in the system, for an arbitrary number of applications. In various implementations, some or all of these steps may be optional, and the order of the steps may be different.

Although FIG. 2C shows a model where applications are pulling data locations from the data discovery service 222, there are alternate models whereby one or more solutions or applications may register with the data discovery service 222 in a subscription model to receive updates to data and the data discovery service 222 may proactively send updates to those applications that are registered and authorized to receive such updates. In some implementations, the data discovery service 222 may notify a resource subscriber when they are no longer authorized to receive updates for a resource.

In some implementations, the one or more applications are reconfigurable based on constraints of the health utility platform 102. A solution may include one or more applications. When participants subscribe to a solution, the one or more applications that comprise the solution may be made available to the participant, such as by installing the application executable into the participant's landing zone. A solution may include one or more smart contracts. The smart contracts may be made available to the participant by configuring and enabling the smart contract to run in the participant's blockchain node. An application may be reconfigured for one of a number of reasons, such as a newer version becoming available, or if the application needs to maintain a list of all subscribers, then the list of subscribers may be updated.

Example Look-Up or Assignment for a Provider

Figure 3A:
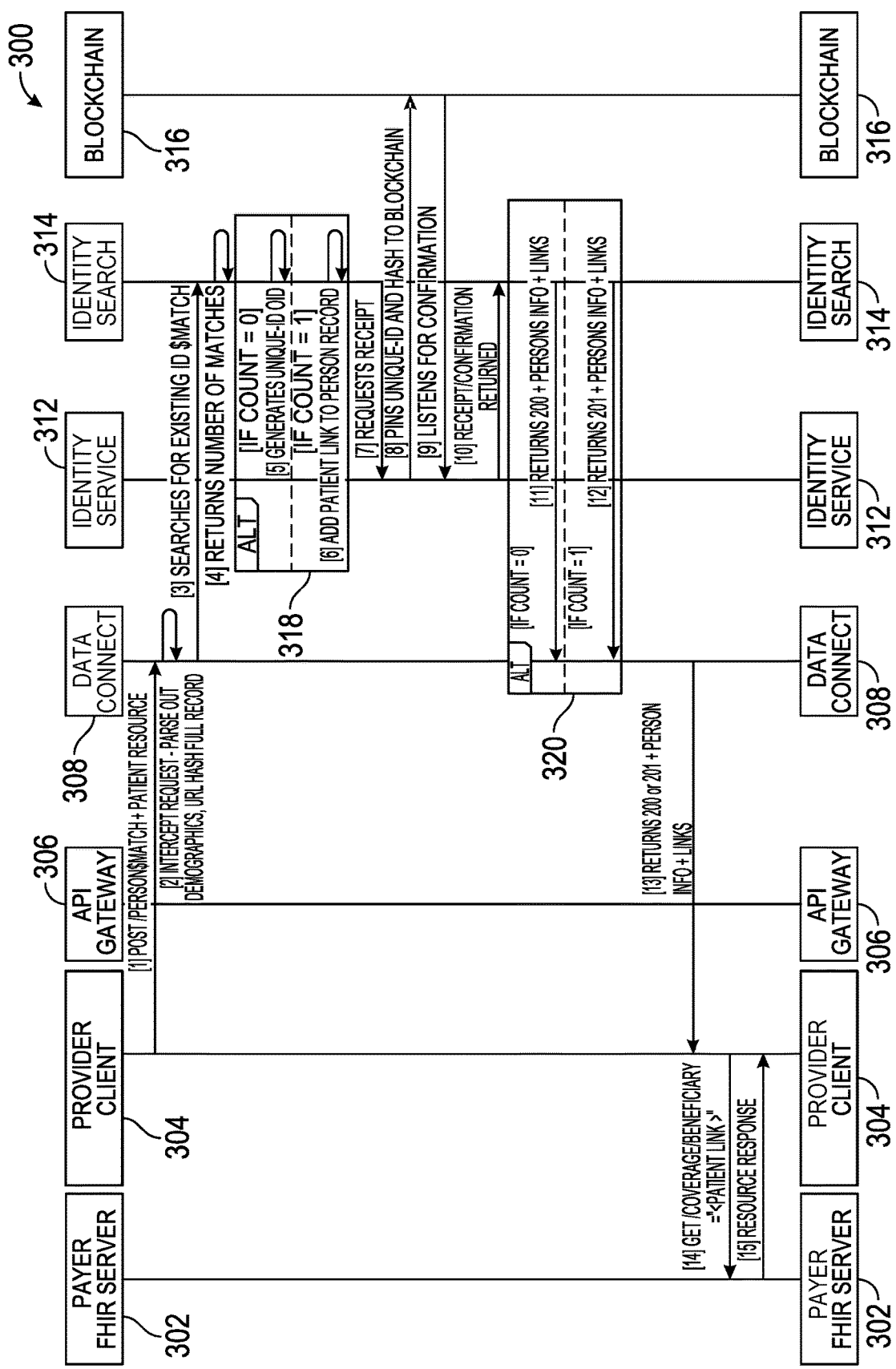
FIG. 3A shows a sequence diagram for an example process for identifier look-up or assignment for a provider and subsequent request by the provider to the payer for related data, according to some implementations.

FIG. 3A shows a sequence diagram for an example process 300 for identifier look-up or assignment for a provider, according to some implementations. In some implementations, a provider client 304 (e.g., the participant application 112) posts (1) a person match request and a request for resources for the patient via an API gateway. A Data Connect 308 intercepts (2) the request and parses out demographics and hashes the full record. The Data Connect 308 searches (3) for existing identifier match by communicating with HUN identity search 314 via the identity service 312, using a message broker for the HUP (e.g., the message broker 228). The HUN identity search 314 returns (4) a number of matches. As shown in the box 318, if the number of matches (COUNT) is 0, then the HUN identity search 314 generates (5) a unique identifier. If COUNT is equal to 1, then the HUN identity search 314 adds (6) a patient link to the record corresponding to the match. The HUN identity search 314 subsequently requests (7) the identity service 312 for a receipt. In response, the identity service 312 pins (8) the unique identifier and adds it and its hash to a blockchain 316. The identity service 312 listens (9) for confirmation from the blockchain 316 and returns (10) a receipt or confirmation to the HUN identity search 314. As indicated in the box 320, the HUN identity search 314 may return (11) a first code (e.g., 200), person's information and relevant links to the Data Connect 308, if COUNT is 0. If COUNT is 1, on the other hand, the HUN identity search 314 returns (12) a different code (e.g., 201), the person's information and relevant links. The Data Connect 308 subsequently returns (13) the code, the person's information and links to the provider client 304. The provider client may use the person's information and links to inquire from the data discovery service 178 the organizations with information related to the person, such as coverage, beneficiary information, clinical records and may (14) get coverage or beneficiary information or other information from a payer FHIR server 302 that responds (15) with resource information. In various implementations, some of the steps described above are optional, and/or the order of the steps may be different.

Example Look-Up or Assignment for a Payer

Figure 3B:
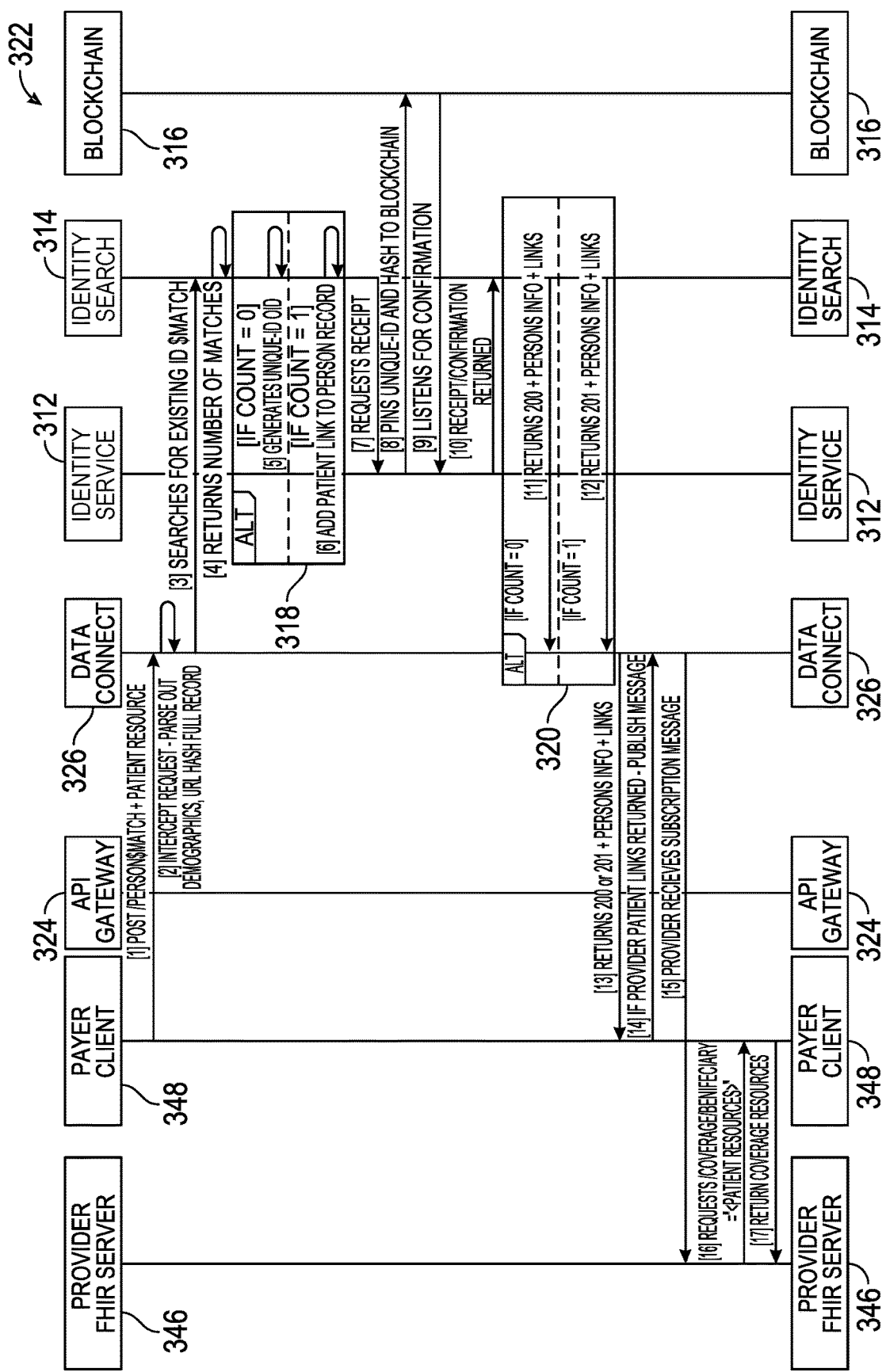
FIG. 3B shows a sequence diagram for an example process for a payer to upload new data and for providers to receive the updated data, according to some implementations.

FIG. 3B shows a sequence diagram for an example process 322 for identifier look-up or assignment for a payer, according to some implementations. Steps (1) to (13) are similar to FIG. 3A so they are not repeated here. The differences are that a payer client 348, instead of the provider client 304 is initiating the process and API gateway 324, and Data Connect 326, corresponding to the payer member, perform operations corresponding to the API gateway 306, and Data Connect 308, respectively. In step (13), the Data Connect 326 returns the code, person's information and links to the payer client 348. In response, the payer client 348 may, if provider patient links were returned, publish (14) message to the Data Connect 326. The Data Connect 326 may send (15) subscription message to a provider FHIR server 346 indicating an update to a subscribed resource. The provider FHIR server 346 may, in response, request (16) coverage or beneficiary or clinical information from the payer client 348 which may return (17) coverage or other resources back to the provider FHIR server 346. In various implementations, some of the steps described above are optional, and/or the order of the steps may be different.

Example Bulk Update

Figure 3C:
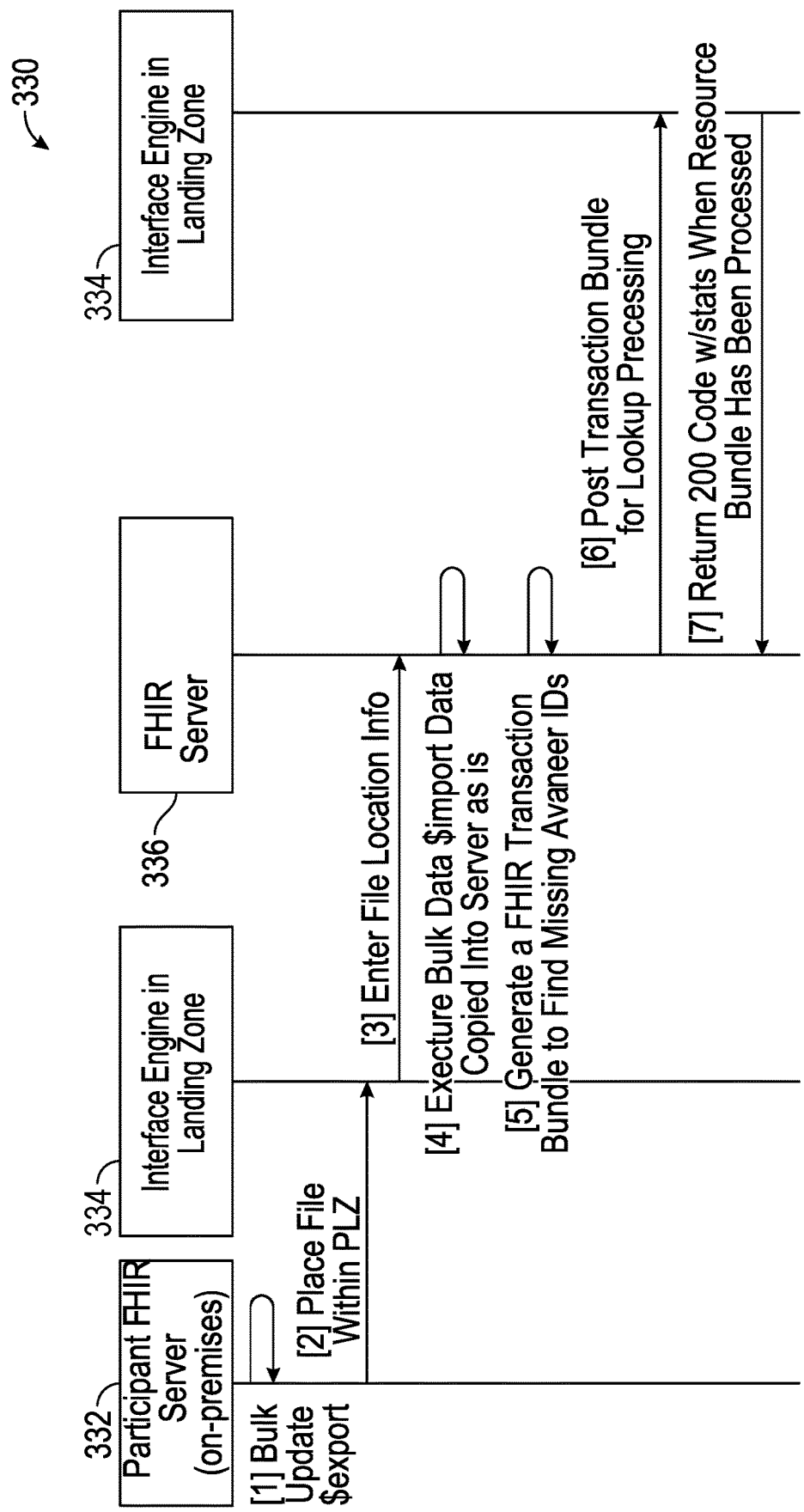
FIG. 3C shows a sequence diagram for an example process for bulk update, according to some implementations.

FIG. 3C shows a sequence diagram for an example process 330 for bulk update, according to some implementations. In some implementations, a participant FHIR server 332 (outside of participant landing zone, on-premises) initiates (1) a bulk update or export, places (2) file within an interface engine in a participant landing zone 334. The interface engine 334 enters (3) file location information into a FHIR server 336 which in turn executes (4) bulk data import data copied into server as-is, and generates (5) a FHIR transaction bundle to find missing unique member identifiers. The FHIR server 336 also posts (6) transaction bundle to the interface engine 334 for look-up processing. The interface engine 334 returns (7), to the FHIR server 336, a predefined code with statistics when resource bundle has been processed. In various implementations, some of the steps described above are optional, and/or the order of the steps may be different.

Example Payer-Provider Coverage Update

Figure 3D:
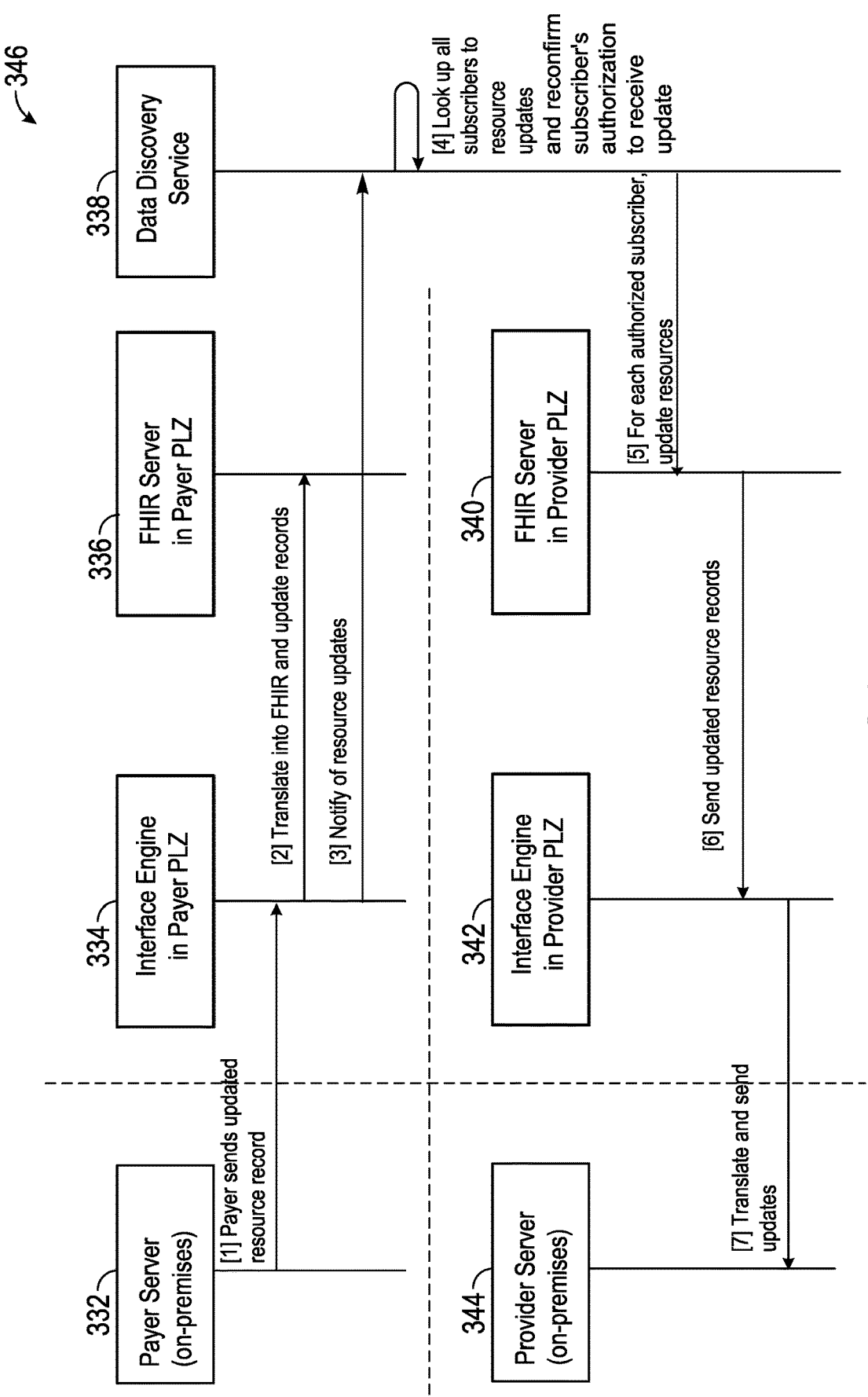
FIG. 3D shows a sequence diagram for an example process for payer-provider resource update, according to some implementations.

FIG. 3D shows a sequence diagram for an example process 346 for a payer-provider resource update service, such as for coverage, benefit, or clinical resources, according to some implementations. (1) The payer server 332 sends updated resources to the interface engine 334 in the payer's participant landing zone. (2) The interface engine 334 translates the resource data into FHIR format and updates the FHIR server in payer PLZ 336. (3) The interface engine 334 notifies the data discovery service 338 of resource updates. (4) The data discovery service 338 looks up subscribers to the updated resources, confirms authorization to receive updates. (5) For each authorized subscriber, the data discovery service 338 sends updated resources to FHIR servers in the one or more provider PLZs 340. (6) The FHIR server 340 sends updated resource record to the interface engine in provider PLZ 342. (7) The interface engine in provider PLZ 342 translates FHIR resource and sends updates to a provider server 344. In some implementations, the data discovery service 338 may send (not shown in FIG. 3D) a notification to a subscriber that they are no longer authorized to receive updates for a specific resource. In various implementations, some of the steps described above are optional, and/or the order of the steps may be different.

Example Operations of a Health Network Manager

Figure 5:
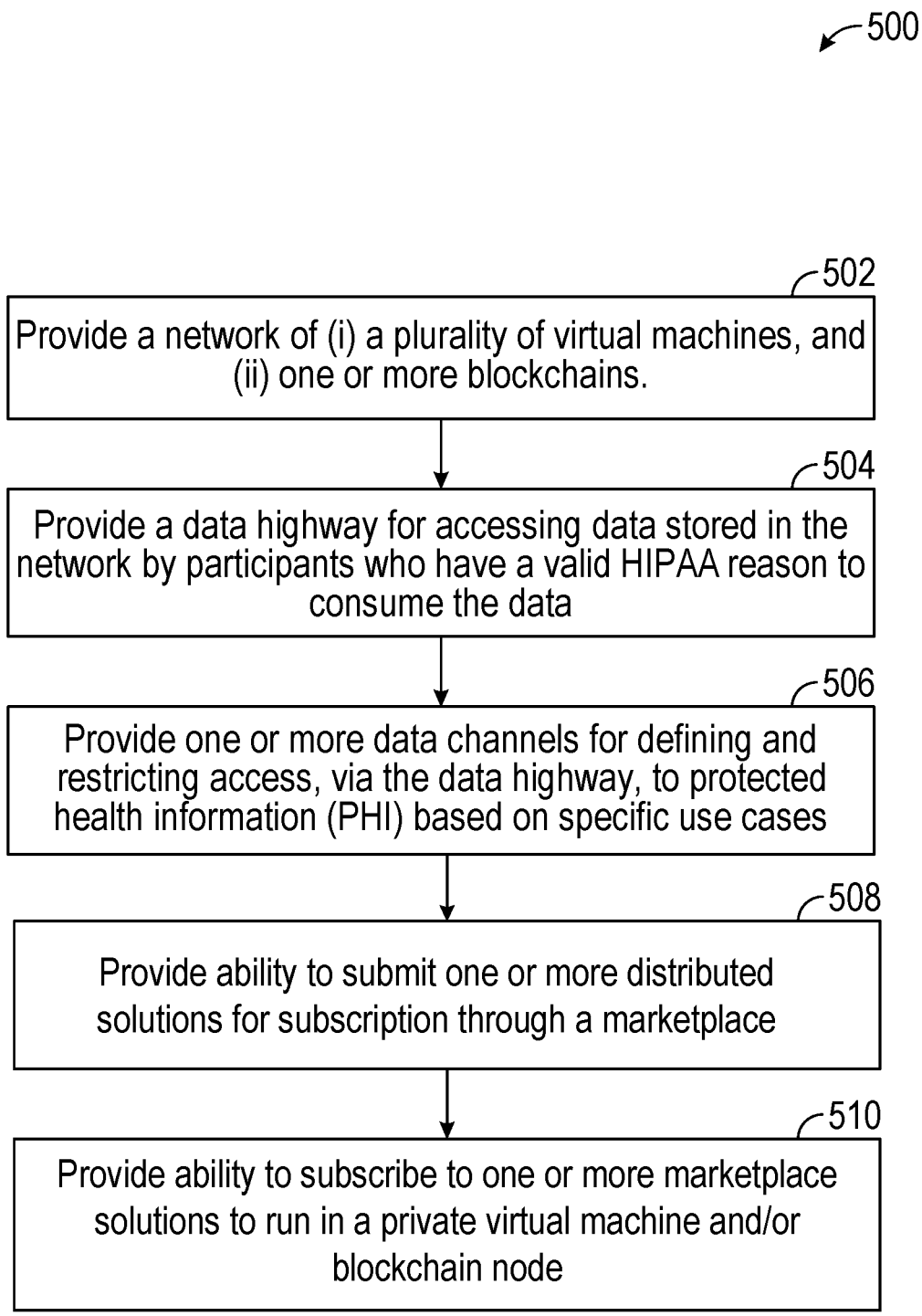
FIG. 5 shows an example method for managing a health utility network, according to some implementations.

FIG. 5 shows an example method 500 for managing a health network, according to some implementations. The method may be performed by a health utility network manager (e.g., the HUN manager 130). The method includes providing (502) a network of (i) a plurality of virtual machines (e.g., the participant landing zones 234 and 254 in FIG. 2A configured in a virtual private cloud may be virtual machines), and (ii) one or more blockchains (e.g., blockchain service 268). Each blockchain includes one or more blockchain nodes (e.g., the peer nodes 188, 190 and 192) for pinning transaction hashes and storing network or other configuration data, and for running smart contracts. The method also includes providing (504) a data highway for accessing data stored in the network by participants who have a valid HIPAA reason to consume the data. The participants are communicatively connected to the network via a subset of the plurality of virtual machines. The method also includes providing (506) one or more data channels for defining and restricting access, via the data highway, to protected health information (PHI) based on specific use cases. In some implementations, the method further includes providing (508) an ability to submit one or more distributed solutions for subscription through a marketplace. In some implementations, the method further includes providing (510) an ability to subscribe to one or more marketplace solutions to run in a private virtual machine and/or a blockchain node. In some implementations, the method further includes: receiving a transaction from a first virtual machine of the plurality of virtual machines. The transaction often corresponds to a member of a participant; searching for a member identifier and associated metadata for the member corresponding to the transaction; authorizing the transaction to transmit using the data highway; and transmitting data corresponding to the transaction to a second virtual machine of the plurality of virtual machines, based on the authorization. In some implementations, the method further includes recording a hash of the transaction on the one or more blockchain nodes. These steps may be performed by components of the HUP 102, the health network 106 and/or the HUN manager 130. In some implementations, each virtual machine includes respective compute and storage environments. In some implementations, each virtual machine is configured to execute one or more decentralized applications sourced from a managed solution repository. In some implementations, one or more participants subscribe to the one or more decentralized applications, the one or more decentralized applications are enabled in each subscriber's landing zone, and a decentralized application is able to communicate directly with a similar instance of itself in any other landing zone. This is a significant differentiator with the mobile application (app) environment as app-to-app communication (such as messaging apps) always require a central server as the intermediary. In some implementations, a first set of decentralized applications of the one or more decentralized applications provides one or more services to a second set of decentralized applications of the one or more decentralized applications (e.g., as building blocks of a compound solution). In some implementations, the one or more decentralized applications in a landing zone share data using a FHIR Server or other database tables in the landing zone (share data between the applications in a non-siloed manner). In some implementations, each virtual machine is configured to store data in a common format with common access means. For example, the data sent to a landing zone may be in FHIR format or in some other format. In the latter case, the data will be reformatted to conform to the FHIR data standards. Once in FHIR format, the data is stored in a FHIR server in the same landing zone. Access to the data by a solution will be through the same authorization method for each participant.

In some implementations, the method further includes providing one or more collaboration services that includes an identity service for generating a unique identifier for each patient or health plan member, based on deterministic and/or probabilistic matching. In some implementations, the one or more collaboration services include a data discovery service for providing a FHIR resource-based directory service for identifying locations of data corresponding to a member. In some implementations, the method further includes providing one or more collaboration services that includes a workflow authorization service for performing authorization based on a plurality of levels of granularity, including data source, resource type and requesting entity.

In another aspect, a method may be provided for obtaining a member identifier for a member, by a first landing zone of a plurality of landing zones. Each landing zone includes respective compute and storage environments and is communicatively coupled to other landing zones via a network. The method also includes searching the network for data for the member using the member identifier to obtain identifiers corresponding to one or more landing zones that have the data or inquiring a data discovery service which keeps track of the participants with data associated to a specific member identifier. The method also includes selecting a second landing zone from the one or more landing zones. The method also includes transmitting a request to the second landing zone for requesting transactions to be executed on the data local to each landing zone thereby causing the second landing zone to (i) authenticate and authorize the request using identity and access management and a workflow authorization server, and (ii) transmit the data or the result of executing the transaction on the local copy of the data to the first landing zone. The method also includes receiving the data or result from the second landing zone. In some implementations, the authentication and/or authorization uses ledger identities. In some implementations, transmitting the request to the second landing zone further causes the second landing zone to cause a smart contract running on the distributed ledger service to pin a hash of the request on a blockchain using cryptographic hashes. In some implementations, each landing zone is communicatively coupled to a respective on-premises system that provides or consumes data and/or internal services. In some implementations, each landing zone is communicatively coupled to one or more cloud services.

In some implementations, a solution that is deployed in more than one PLZ may work collaboratively with the other deployments of the same solution to submit a request to a parallel solution to perform a task directly on the data in the FHIR server in that PLZ, obviating the need for transmitting the data from the second PLZ to the first PLZ. For some solutions this ability to tap into the compute resources of the other PLZs and to not replicate the data has the potential to reduce the time needed to complete a task and to reduce the replication of data.

With dynamic information updates on the network, participants may be informed and/or use the updates using a single connection to the HUN 100. The example provided in the Background section may be used to illustrate the power of the techniques described in this disclosure.

Question: Who is this patient?
Answer: Verified Patient: AW35 6ZRZ 45TZ R3ED . . . (Following patient release of their record)
Question: Is the patient currently covered?
Answer: YES, Health Care Voluntary Plans, HMO, fully insured, effective 01/01/2021 through 12/31/2021; At one time, the patient did have coverage through Good Care Health Plan.
Question: What are the patient's medications, labs, imaging, and clinical history?
Answer: YES, Good Clinic, Autoimmune Thyroiditis, Chronic, Currently prescribed Levothyroxine 150 mcg. Links to detailed labs and images provided here as FHIR resources.

With the HUN 100 enabled eligibility check, current data may already exist in a provider's system due to the proactive data updating in response to a subscription request. When data changes, the data associated with that unique member identifier may be automatically provided to the subscribed participant for their review and updating in their system. Participants may opt for the updates to be applied without a review step. Whether the update is from a payer or provider, or other approved organization, the data is always made current within a short period of time. A provider may need to share a patient's demographic data to either locate the patient's current unique identifier or to have a new identifier created. From that point forward, the HUN 100 may facilitate proactive updates and may provide accurate information, such as eligibility status, as well as other information that is associated with that identifier. Once the unique identifier is created, and/or associated with a patient in a provider's EHR or other system, all subscribed changes (e.g., change in coverage) may be proactively updated for that identifier. All other data that a provider chooses to share with another member (e.g., another provider for coordination of care) may be on a requested basis, via a direct point-to-point connection to the other authorized FHIR server(s) without the data being transferred to an intermediary. There is no data aggregation or exposure by the HUN 100. The data creator owns and controls their data. The HUN 100 act as the private internet built specifically for healthcare. Today's environment is one of multiple, expensive, and varied connections to get the information that is needed. Much of this data lies with data aggregators and may or may not be the most recent and accurate. Each connection is a potential point of failure and presents multiple security challenges. Not to mention, very expensive. With a single connection to the HUN 100, all data that an organization is permissioned to have are made available, and dynamically updated. Meaning that if a change is made to data a provider has subscribed to, the appropriate record is automatically updated by the network ensuring the highest levels of accuracy. The data is there when an organization needs it.

The HUN 100 may provide the network and services that enable interoperability, the common set of tools for solution developers, along with the highest levels of security and privacy. The HUN 100 may enable such solutions as payer-to-payer data exchange, eligibility, real time claims submission and processing, claims editing, and submission of prior authorization requests. The HUN 100 may also have a marketplace where participants as well as independent solution providers can make solutions available on the marketplace for everyone on the network to use if they want to subscribe. As another use case that can be enabled by this system, a payer-to-payer coordination of benefits solution can be enabled where the HUN 100 may provide immediate compliance with the CMS regulation: The 21st Century Cares Act which requires payers to provide five years of coverage data about their current members, even if that member was at a different payer at that time.

Each of the above identified elements may be stored in one or more memory devices and corresponds to a set of instructions for performing a function described above. The above identified modules or programs (i.e., sets of instructions) need not be implemented as separate software programs, procedures, modules or data structures, and thus various subsets of these modules may be combined or otherwise re-arranged in various implementations. In some implementations, the memory may store a subset of the modules and data structures identified above. Furthermore, the memory may store additional modules and data structures not described above.

Reference has been made in detail to implementations, examples of which are illustrated in the accompanying drawings. In the detailed description above, numerous specific details have been set forth in order to provide a thorough understanding of the various described implementations. However, it will be apparent to one of ordinary skill in the art that the various described implementations may be practiced without these specific details. In other instances, well-known methods, procedures, components, circuits, and networks have not been described in detail so as not to unnecessarily obscure aspects of the implementations.

It will also be understood that, although the terms first, second, etc. are, in some instances, used herein to describe various elements, these elements should not be limited by these terms. These terms are only used to distinguish one element from another. For example, a first device could be termed a second device, and, similarly, a second device could be termed a first device, without departing from the scope of the various described implementations. The first device and the second device are both types of devices, but they are not the same device.

The terminology used in the description of the various described implementations herein is for the purpose of describing particular implementations only and is not intended to be limiting. As used in the description of the various described implementations and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" is, optionally, construed to mean "when" or "upon" or "in response to determining" or "in response to detecting" or "in accordance with a determination that," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]" or "in accordance with a determination that [a stated condition or event] is detected," depending on the context.

For situations in which the systems discussed above collect information about users, the users may be provided with an opportunity to opt in/out of programs or features that may collect personal information (e.g., information about a user's preferences or usage of a smart device). In addition, in some implementations, certain data may be anonymized in one or more ways before it is stored or used, so that personally identifiable information is removed. For example, a user's identity may be anonymized so that the personally identifiable information cannot be determined for or associated with the user, and so that user preferences or user interactions are generalized (for example, generalized based on user demographics) rather than associated with a particular user.

Although some of various drawings illustrate a number of logical stages in a particular order, stages that are not order dependent may be reordered and other stages may be combined or broken out. While some reordering or other groupings are specifically mentioned, others will be obvious to those of ordinary skill in the art, so the ordering and groupings presented herein are not an exhaustive list of alternatives. Moreover, it should be recognized that the stages could be implemented in hardware, firmware, software or any combination thereof.

The foregoing description, for purpose of explanation, has been described with reference to specific implementations. For example, the term "may" is used to describe ways in which components are combined in some implementations. However, the illustrative discussions above are not intended to be exhaustive or to limit the scope of the claims to the precise forms disclosed. Many modifications and variations are possible in view of the above teachings. The implementations were chosen in order to best explain the principles underlying the claims and their practical applications, to thereby enable others skilled in the art to best use the implementations with various modifications as are suited to the particular uses contemplated.

What is claimed is:

1. A system comprising:
a health utility platform configured to execute one or more collaboration services and one or more distributed ledger services, wherein the one or more collaboration services include an identity service, a data discovery service, and a workflow authorization service, wherein the one or more distributed ledger services includes a blockchain service;
a health network including a private network interconnect configured to provide access, routing and service discovery, wherein the health network is communicatively coupled to the health utility platform; and
a plurality of landing zones communicatively coupled to the health utility platform via the health network, wherein each landing zone is configured to run one or more applications for a participant, wherein the one or more applications are configured to consume data and/or provide services on the health network,
wherein the one or more collaboration services and the one or more distributed ledger services are configured to provide context, facilitate data exchanges or provide capability for distributed computing between different landing zones of the plurality of landing zones,
wherein a first landing zone includes a solution that includes a first application configured to:
receive a unique identifier for a member from the identity service;
receive one or more FHIR resource locators for the member from the data discovery service using the unique identifier;
transmit a request for the FHIR resource or for a service to be performed on the FHIR resource to a second landing zone based on the one or more FHIR resource locators; and
receive FHIR resource data or a result of executing the request on the FHIR resource data for the member from the second landing zone, and
wherein the second landing zone includes a second FHIR server that is configured to:
receive the request from the first landing zone;
transmit an authorization request to the workflow authorization service for the received request;
receive a response to the authorization request from the workflow authorization service; and
send the FHIR resource data or the result of executing the request on the FHIR resource data from the second FHIR server to the first landing zone.

2. The system of claim 1, wherein each landing zone is configured in a virtual private cloud network, as a set of components running in an environment for running containers.

3. The system of claim 1, wherein at least one landing zone is configured within an on-premises system configured to provide or consume data and/or internal services.

4. The system of claim 1, wherein each landing zone includes at least a cross-platform interface engine, a Health Level Seven (HL7) Fast Healthcare Interoperability Resources (FHIR) server, a data storage, a lightweight web server, an authentication and authorization tool, and access to blockchain services.

5. The system of claim 1, wherein the one or more collaboration services are configured in a virtual private cloud network, as a set of components running in an environment for running containers.

6. The system of claim 1, wherein the one or more distributed ledger services are configured to run on one or more blockchain services.

7. The system of claim 6, wherein each blockchain service includes (i) a first one or more nodes configured to store copies of a blockchain and perform chaincode or smart contract execution and transaction validation and (ii) a second one or more nodes configured to provide an ordering service which determines an ordering of blocks on the blockchain and enforces access controls to channels, wherein a channel is a private blockchain where resources including transactions and smart contracts are private to the channel members.

8. The system of claim 1, wherein the one or more distributed ledger services are configured to run smart contracts and include at least one smart contract for pinning transaction hashes to a blockchain.

9. The system of claim 1, wherein each landing zone is configured to connect with a participant source system for a respective participant via a secure connection, such as a site-to-site VPN connection or a private link connection.

10. The system of claim 1, wherein:
   the one or more collaboration services include an identity service and a data discovery service; and
   each landing zone includes a FHIR server and a cross-platform interface engine configured to:
      receive a data file from a participant data source for a member;
      call an endpoint in the identity service to register the member based on one or more attributes in the data file that indicate demographics for the member;
      receive a unique identifier for the member from the identity service;
      map the data file to a FHIR resource for the data file;
      store data corresponding to the data file in the FHIR server based on the FHIR resource;
      receive one or more resource locators from the FHIR server for the stored data; and
      register the one or more resource locators with the data discovery service.

11. The system of claim 1, wherein:
   the first application is further configured to:
      call a first endpoint in the identity service to search for the member; and
      call a second endpoint in the data discovery service using the unique identifier.

* * * * *